United States Patent
Martin (10) Patent No.: US 11,458,114 B2
(45) Date of Patent: Oct. 4, 2022

(54) METHODS AND COMPOSITIONS FOR ENHANCING SYNTHESIS SECRETION AND TRANSPORT OF COLLAGEN TO INCREASE WOUND STRENGTH

(71) Applicant: Alain Martin, Flemington, NJ (US)

(72) Inventor: Alain Martin, Flemington, NJ (US)

(73) Assignee: NORTH CELL PHARMACEUTICALS, INC., Flemington, NJ (US)

( * ) Notice: Subject to any disclaimer, the term of this patent is extended or adjusted under 35 U.S.C. 154(b) by 123 days.

(21) Appl. No.: 16/873,603

(22) Filed: May 19, 2020

(65) Prior Publication Data

US 2021/0361604 A1 Nov. 25, 2021

(51) Int. Cl.
| | |
|---|---|
| *A61K 31/198* | (2006.01) |
| *A61K 31/401* | (2006.01) |
| *A61P 17/02* | (2006.01) |
| *A61K 9/08* | (2006.01) |
| *A61K 45/06* | (2006.01) |

(52) U.S. Cl.
CPC .............. *A61K 31/198* (2013.01); *A61K 9/08* (2013.01); *A61K 31/401* (2013.01); *A61P 17/02* (2018.01); *A61K 45/06* (2013.01)

(58) Field of Classification Search
CPC ..................................................... A61K 31/198
See application file for complete search history.

(56) References Cited

U.S. PATENT DOCUMENTS

| | | | | |
|---|---|---|---|---|
| 5,716,926 A | * | 2/1998 | Beale ................... | A61K 31/415 514/3.8 |
| 7,122,578 B2 | * | 10/2006 | Martin .................. | A61K 31/56 514/560 |

OTHER PUBLICATIONS

Debats et al. Nitric Oxide, 2009, 21(3-4): 175-83 (abstract).*

* cited by examiner

*Primary Examiner* — Rei Tsang Shiao (57) ABSTRACT

A method for, and medicinal composition for, treatment of mammalian cells for enhancing synthesis, secretion and transport of collagen to increase wound strength, that includes magnesium pyruvate; calcium pyruvate; L proline; citrulline: and a liquid carrier.

16 Claims, 1 Drawing Sheet

METHODS AND COMPOSITIONS FOR ENHANCING SYNTHESIS SECRETION AND TRANSPORT OF COLLAGEN TO INCREASE WOUND STRENGTH

REFERENCE TO RELATED APPLICATIONS

The present application has no related pending patent applications.

BACKGROUND OF INVENTION

Field of Invention

The present invention relates to a method and composition for enhancing the synthesis, secretion and transport of collagen, adhesion molecules and elastin to wound sites needed to increase wound strength, wound texture and pigmentation. This invention has demonstrated that a certain combination of salts of pyruvate with L proline and citrulline were synergistic and enhanced the synthesis, secretion and transport of collagen, adhesion molecules, and elastin to wound sites that increased wound strength, wound texture and pigmentation.

Description of Related Art

The following outlines the present invention and the history of various prior art treatments and patents are representative of the field pertaining to the present invention:

The present invention has demonstrated that a certain combination of salts of pyruvate with L proline and citrulline were synergistic and enhanced the synthesis, secretion and transport of collagen, adhesion molecules, and elastin to wound sites that increased wound strength, wound texture and pigmentation. The combination of calcium pyruvate and magnesium pyruvate with the addition of L proline and L-citrulline enhanced membrane synthesis, secretion and transport type 1 collagen, cellular adhesion molecules, and elastin at wound sites that increase wound strength, wound texture and pigmentation. The magnesium and calcium salts of pyruvate, with L proline and L citrulline (SRF—Skin resuscitation Factor) was superior over standard and current sodium pyruvate wound healing products and formula. The use of this formula (SRF) clearly demonstrated that it can be used to produce better efficacy in patients with wrinkles, aging skin, cellulitis, wounds and diseases which are selected from the group consisting of infected and noninfected wounds, bacterial infections, fungal infections, cellulite, viral infections, cold sores, thermal burns, sunburns, chemical burns, surgical wounds, psoriasis, eczema, decubitus ulcers, cancer, diabetic ulcers, dermatoses, inflammatory diseases, and wounds resulting from laser treatment, micro-wounded skins, scratches, micro-needling, abrasions, laceration, puncture, dry skin, contact with irritants, contact with allergens or other substances that are harmful to skin or skin cells.

Membrane transport systems are the key to the synthesis, secretion and transport of key molecules to maintain health for all organs and to enhance wound repair and increase wound strength, texture and pigmentation. Wounds are internal or external bodily injuries or lesions caused by mechanical, chemical, viral, bacterial or thermal means, which disrupt the normal continuity of structures. Such bodily injuries include contusions, which are wounds in which the skin is unbroken; incisions, i.e., which are wounds in which the skin is broken by a cutting instrument; and lacerations, which are wounds in which the skin is broken by a dull or blunt instrument. Membrane transport systems are the key to the synthesis and secretion of key molecules to maintain health for all organs and to enhance wound repair and wound strength, texture and pigmentation. Most wounds also produce pain, swelling, itching, ischemia, crusting, erythema, scarring and all wounds loose wound strength, texture and pigmentation. The rate of healing, (reepithialization) does not necessarily correlate with wound strength, texture or pigmentation. You can have a wound that heals quickly, but has low wound strength allowing the wound to reopen again and again.

Wound strength: Cell Adhesion Molecules (CAMs) are proteins located on the cell surface involved with the binding with other cells or with the extracellular matrix (ECM) in the process called cell adhesion that enhance healing and wound strength. Essentially, cell adhesion molecules help cells stick to each other and to their surroundings. These proteins are typically transmembrane receptors and are composed of three domains: an intracellular domain that interacts with the cytoskeleton, a transmembrane domain, and an extracellular domain that interacts either with other CAMs of the same kind (homophilic binding) or with other CAMs or the extracellular matrix (heterophilic binding).

Most of the CAMs belong to four protein families: Ig (immunoglobulin) superfamily (IgSF CAMs), the integrins, the cadherins, and the selectins. One classification system involves the distinction between calcium-independent CAMs and calcium-dependent CAMs. The Integrins are a family of heterophilic CAMs that bind IgSF CAMs or the extracellular matrix. They are heterodimers, called alpha and beta. Eighteen different alpha subunits that combine with 8 different beta subunits to form twenty-four known integrins; however not all combinations are observed. The cadherin's are a family of homophylic CAMs, $Ca^{2+}$-dependent.

Melanocytes are melanin-producing cells located in the bottom layer of the skin's epidermis, the middle layer of the eye (the uvea), the inner ear, bones, and heart. Melanin is the pigment primarily responsible for skin color. Once synthesized, melanin is contained in a special organelle called a melanosome and moved along arm-like structures called dendrites, so as to reach the keratinocytes. Through a process called melanogenesis, these cells produce melanin, which is a pigment found in the skin, eyes, and hair. This melanogenesis leads to a long-lasting pigmentation, which is in contrast to the pigmentation that originates from oxidation of already-existing melanin.

One of fibroblasts' most important duties is the production of collagen. Collagen deposition is important because it increases the strength of the wound; before it is laid down, the only thing holding the wound closed is the fibrin-fibronectin clot, which does not provide much resistance to traumatic injury. Also, cells involved in inflammation, angiogenesis, and connective tissue construction attach to, grow and differentiate on the collagen matrix laid down by fibroblasts. Type III collagen and fibronectin are generally beginning to be produced in appreciable amounts at somewhere between approximately 10 hours and 3 days, depending mainly on wound size. Their deposition peaks at one to three weeks. They are the predominating tensile substances until the later phase of maturation, in which they are replaced by the stronger type I collagen. Even as fibroblasts are producing new collagen, collagenases and other factors degrade it. Shortly after wounding, synthesis exceeds degradation so collagen levels in the wound rise, but later production and degradation become equal so there is no net collagen gain. This homeostasis signals the onset of the later maturation phase. Granulation gradually ceases and fibroblasts decrease in number in the wound once their work is done. At the end of the granulation phase, fibroblasts begin to commit apoptosis, converting granulation tissue from an environment rich in cells to one that consists mainly of collagen. Mitochondria have a direct impact on the synthesis of cellular adhesion molecules and collagen. Increasing the synthesis of collagen is also a critical aspect of decreasing wrinkles.

Elastin, which is not collagen, is a highly elastic protein in connective tissue and allows many tissues in the body to resume their shape after stretching or contracting. Elastin helps skin to return to its original position when it is poked or pinched. Elastic fiber is composed mainly of an amorphous component, which is extensively cross-linked elastin, and a fibrillar component, which are primarily the microfibrils such as fibrillin, both of which are made of simple amino acids such as glycine, valine, alanine, and proline.

Eczema or atopic dermatitis is a form of dermatitis, or inflammation of the epidermis (the outer layer of the skin). These types of diseases all suffer from weak wound strength. The term eczema is broadly applied to a range of persistent skin conditions. These include dryness and recurring skin rashes that are characterized by one or more of these symptoms: redness, skin edema (swelling), itching and dryness, crusting, flaking, blistering, cracking, oozing, or bleeding. Areas of temporary skin discoloration may appear and are sometimes due to healed injuries. Scratching open a healing lesion may result in scarring and may enlarge the rash.

The type of eczema may be described by location (e.g., hand eczema), by specific appearance (eczema craquele or discoid), or by possible cause (varicose eczema). Further adding to the confusion, many sources use the term eczema for the most common type of eczema (atopic dermatitis) interchangeably. The classifications below is ordered by incidence frequency. Atopic eczema, Contact dermatitis, Xerotic eczema, Seborrheic dermatitis, Dyshidrosis, Discoid eczema, Venous eczema, Dermatitis herpetiformis, Neurodermitis, Autoeczematization. Eczema can be exacerbated by dryness of the skin. Moisturizing is one of the most important self-care treatments for eczema.

Decubitus ulcers, Pressure ulcers, also known as pressure sores, bedsores and decubitus ulcers, are localized injuries to the skin and/or underlying tissue that usually occur over a bony prominence as a result of pressure, or pressure in combination with shear and/or friction. The most common sites are the skin overlying the sacrum, coccyx, heels or the hips, but other sites such as the elbows, knees, ankles or the back of the cranium can be affected.

Pressure ulcers occur due to pressure applied to soft tissue resulting in completely or partially obstructed blood flow to the soft tissue. Shear is also a cause, as it can pull on blood vessels that feed the skin. Pressure ulcers most commonly develop in individuals who are not moving about, such as being bedridden or are confined to a wheelchair. It is widely believed that other factors can influence the tolerance of skin for pressure and shear, thereby increasing the risk of pressure ulcer development. These factors are protein-calorie malnutrition, microclimate (skin wetness caused by sweating or incontinence), diseases that reduce blood flow to the skin, such as arteriosclerosis, or diseases that reduce the sensation in the skin, such as paralysis or neuropathy. The healing of pressure ulcers may be slowed by the age of the person, medical conditions (such as arteriosclerosis, diabetes or infection), smoking or medications such as anti-inflammatory drugs.

External pressure applied over an area of the body, especially over the bony prominences can result in obstruction of the blood capillaries, which deprives tissues of oxygen and nutrients, causing ischemia (deficiency of blood in a particular area), hypoxia (inadequate amount of oxygen available to the cells), edema, inflammation, and, finally, necrosis and ulcer formation. In all pressure ulcers, especially in decubitus ulcers, cellular adhesion molecules are produced at low levels and wound strength never occurs due to the inhibition and damage done to mitochondria and the inability of mitochondria to synthesize membrane phospholipids needed to enhance the synthesis of cellular adhesion molecules, collagen deposition and wound strength.

Aging Skin. Aging of skin is an intricate biological process consisting of two types. While intrinsic or chronological aging is an inevitable process, photoaging involves the premature aging of skin occurring due to cumulative exposure to ultraviolet radiation. Chronological and photoaging both have clinically differentiable manifestations. Skin aging is influenced by several factors including genetics, environmental exposure (UV radiation, xenobiotics, and mechanical stress), hormonal changes and metabolic processes (generation of reactive chemical compounds such as activated oxygen species, sugars and aldehydes). All factors together act on the alterations of skin structure, function, and appearance. Yet solar UV radiation unquestionably is the single major factor responsible for skin aging. Clinically, the intrinsically aged skin is atrophic, which may result in prominence of vasculature and loss of elasticity. The stratum corneum remains relatively unchanged but the epidermis thins with a flattening of the dermo-epidermal junction expressing an increased fragility of the skin. There is considerable decrease in dermal thickness and vascularity as well as a reduction in the number and biosynthetic capacity of the fibroblast resulting in delayed wound healing, loss of wound strength and texture. With an increasing age, there is a progressive decline in the response of keratinocytes and fibroblasts to growth factors, decreasing the proliferative capacity.

Photoaging is the superimposition of photodamage on intrinsically aged skin generally bringing about premature aging. This specific damage occurs by chronic (multiple) exposure of the skin to UV light. Clinically, the skin becomes coarse; epidermis thickens (hyperplasia) initially and then thins (atrophy), there is laxity, sallowness with wrinkles, irregular hyperpigmentation, lentigines, and telangiectasias, acrochordon, and ruby spots), "premalignant" lesions (actinic keratosis, lentigo maligna), and malignant lesions (basal and squamous cell carcinomas and malignant melanomas) on chronically exposed skin found in the face, hands and neck regions. Blood vessels become dilated and twisted (telangiectasia) and finally very sparse, while their walls are initially thickened and later thinned. UV irradiation of the skin increases the reactive oxygen species and decreases the endogenous antioxidant enzymes. This increased production of ROS alters gene and protein structure and function leading to skin damage.

Various natural and synthetic retinoids have been explored for the treatment of aging and many of them have shown histological and clinical improvement, but most of the studies have been carried out in patients presenting with photoaged skin. Retinol family comprises vitamin A (retinol) and its natural derivatives such as retinaldehyde, retinoic acid, and retinyl esters, as well as a large number of synthetic derivatives. Retinoids are required for a vast number of biological processes. In particular, they are involved in embryogenesis, reproduction, vision, growth, inflammation, differentiation, proliferation, and apoptosis. Retinal is an essential part of the rhodopsin pigment, necessary for visions. Retinoids are found in the keratinocytes in two forms: retinol and retinyl esters—probably the storage form. Although retinoids show promise in the treatment of skin aging, irritant reactions such as burning, redness, dryness, swelling, crusting, blistering, scaling or dermatitis associated with retinoid therapy limit their acceptance by patients.

U.S. Pat. No. 5,296,370, issued to Martin, et al., discloses therapeutic compositions for preventing and reducing injury to mammalian cells and increasing the resuscitation rate of injured mammalian cells. In one embodiment, the therapeutic composition comprises (a) a pyruvate, (b) an antioxidant, and (c) a mixture of saturated and unsaturated fatty acids.

U.S. Pat. No. 5,863,938, issued to Martin, discloses a therapeutic antibacterial wound-healing composition comprising an effective amount of an antibacterial agent and a wound-healing composition consisting of (a) pyruvate (b) an antioxidant, and (c) a mixture of fatty acids. This patent teaches the use of pyruvate, vitamin E and fatty acids to treat wounds.

U.S. Pat. No. 7,122,578 (Martin) discloses a method for treating wounds, injuries, diseases and dermatological disease states in mammals caused by mammalian cells involved in the inflammatory response comprising contacting the mammalian cells with an antioxidant reactive oxygen species mediator selected from the group consisting of .alpha.-keto acids used singly or in combination in an amount capable of reducing the undesired inflammatory conditions. The only combination of alpha keto acids shown to be synergistic was pyruvate with alpha keto isovalerate with fatty acids.

U.S. Pat. No. 8,076,373 (Martin) teaches the use of alpha keto acids to protect drugs such as antivirals, antibacterials, antifungals, and anticancer drugs that are attacked by oxygen radicals especially peroxynitrite. In this patent the use of pyruvate with other keto acids without vitamin E and fatty acids was shown to protect drugs form peroxynitrite.

The patented therapeutic compositions listed above report the use alpha keto acids as antioxidants that neutralize the negative effects of reactive oxygen radicals (sodium pyruvate, alpha ketoglutarate, keto isovalerate and vitamin E) at wound sites, with the addition of fatty acids for membrane repair, which enhance the rate of wound healing.

Enhancing the rate of wound healing does not guarantee an increase in wound strength, texture, elasticity and pigmentation at wound sites. None of the compositions or inventions to date provide a method for enhancing the synthesis of key adhesion molecules, skin phospholipids, elastin and type 1 collagen, that increases wound strength, texture and pigmentation. By using the synergistic combination of calcium pyruvate, magnesium pyruvate, in combination with the correct concentrations and ratios of L proline and L-citrulline (SRF) the transport and synthesis of adhesion molecules, phospholipids, elastin and type 1 collagen, increased wound strength, wound texture and pigmentation, while decreasing wound scars. Also, SRF increased the synthesis of Collagen to eliminate wrinkles, increased wound strength, wound texture and pigmentation.

The disclosures referred to herein to illustrate the background of the invention and to provide additional detail with respect to its practice are incorporated herein by reference and, for convenience, are referenced in the following text and respectively grouped in the appended bibliography.

SUMMARY OF THE INVENTION

The present invention is directed to a medicinal composition for treatment of mammalian cells, comprising: magnesium pyruvate; calcium pyruvate; L proline; citrulline: and, a liquid carrier. In some embodiments of the present invention medicinal composition, the magnesium pyruvate and the calcium pyruvate are each in the amount of about 0.1% to about 5.0%, based on total weight of the composition. In some preferred embodiments, the magnesium pyruvate and the calcium pyruvate are each in the amount of about 0.2% to about 4.0%, based on total weight of the composition. In some embodiments, magnesium pyruvate and the calcium pyruvate are each in the amount of about 0.5% to about 4.0%, based on total weight of the composition. In some embodiments of the present invention medicinal composition, the L proline and the citrulline are each in the amount of about 0.1% to about 3.0%, based on total weight of the composition. In some embodiments, the L proline and the citrulline are each in the amount of about 0.2% to about 2.5%, based on total weight of the composition. In some embodiments, the citrulline is selected from the group consisting of L citrulline, citrulline malate and combinations thereof. In some embodiments, the composition has a carrier selected from the group consisting of water, oil, water-based carriers, oil-based carriers, gels, emulsions, lotions, creams, solutions and petrolatum. In some embodiments, there is at least one additional active constituent that is selected from the group consisting of antioxidants, antibacterial agents, alpha keto acids, antiviral agents, antifungal agents, antihistamine agents, cancer drugs, IV drugs non-steroidal anti-inflammatory agents, antioxidant agents, fatty acids, steroids, and mixtures thereof. In some embodiments, the alpha-keto acids have four or more carbon atoms and are selected from the group consisting of oxaloacetate, alpha-keto-glutarate, alpha-keto-isovalerate, alpha keto-butyric acid, alpha keto-adipic acid, alpha-keto-caproic acid, salts thereof, and mixtures thereof. In other embodiments, the present invention is a method utilizing the components described herein in this paragraph. Thus, the present invention treatment method for treatment of mammalian cells for enhancing the synthesis of collagen, adhesion molecules, and elastin to increase wound strength, wound texture, pigmentation and nitric oxide, wherein the wounds and diseases are selected from the group consisting patients with wrinkles, aging skin, cellulitis, wounds and diseases which are selected from the group consisting of infected and noninfected wounds, bacterial infections, fungal infections, viral infections, cold sores, thermal burns, sunburns, chemical burns, surgical wounds, psoriasis, eczema, decubitus ulcers, cancer, diabetic ulcers, dermatoses, inflammatory diseases, and wounds resulting from laser treatment, micro-wounded skins, scratches, micro-needling, abrasions, laceration, puncture, dry skin, contact with irritants, contact with allergens or other substances that are harmful to skin or skin cells, involves applying a therapeutically effective amount of a medicinal composition to mammalian cells, the medicinal composition including: a) magnesium pyruvate; b) calcium pyruvate; c) L proline; d) citrulline: and, e) a liquid carrier. The various embodiments of the constituents are described above in this paragraph.

DETAILED DESCRIPTION OF THE INVENTION

The present invention provides a method for enhancing the synthesis, secretion and transport of key components including adhesion molecules, elastin and type 1 collagen to increase wound strength, texture and pigmentation, by forcing fibroblasts to synthetize the correct type of collagen that will reduce scar formations and to stimulate melanocytes to synthesize melanin. The composition method also enhances the production of phospholipids needed to protect mitochondria and cells. The method comprises contacting the mammalian cells with a therapeutically effective amount of the synergistic mixture, wherein the synergistic mixture is selected from the group consisting of certain salts of pyruvates, magnesium and calcium, L proline and L-citrulline (this formula is called Skin Resuscitation Factor (SRF)) wherein the treatment results in the up regulation, transport and synthesis of key components of cellular membranes that enhance wound strength, wound texture and pigmentation at wound sites. Magnesium and calcium, are an essential element in biological systems. Magnesium occurs typically as the $Mg^{2+}$ ion. It is an essential mineral nutrient (i.e., element) for life and is present in every cell type in every organism. For example, ATP (adenosine triphosphate), the main source of energy in cells, must be bound to a magnesium ion in order to be biologically active. What is called ATP is often actually Mg-ATP. As such, magnesium plays a role in the stability of all polyphosphate compounds in the cells, including those associated with the synthesis of DNA and RNA. Over 300 enzymes require the presence of magnesium ions for their catalytic action, including all enzymes utilizing or synthesizing ATP, or those that use other nucleotides to synthesize DNA and RNA. Thus, the calcium and magnesium pyruvate are essential to this process, not sodium pyruvate or any of the other salts of pyruvate to enhance the synthesis, secretion and transport of key components including adhesion molecules, elastin and type 1 collagen to increase wound strength, texture and pigmentation, and healing. The rate of healing, (reepithelization) does not necessarily correlate with wound strength, texture or pigmentation. You can have a wound that heals quickly, but has low wound strength allowing the wound to reopen again and again.

Previous data from previous experiments demonstrated that alpha-keto acids can mitigate the damage produced from the toxic drug by-products caused by oxygen radicals including peroxynitrite, and can decrease the inflammatory process, speed healing and increase the efficacy of the drug at the wound site. Unexpectedly, the combination of calcium pyruvate and magnesium pyruvate with L proline and L-citrulline (SRF) were synergistic in enhancing membrane transport systems to increase the synthesis, secretion and transport of cellular molecules including adhesion molecules, skin phospholipids, elastin and type 1 collagen that enhanced re-epithelization, wound strength, wound texture and pigmentation. All combinations of sodium pyruvate with alpha keto-butyric acid, alpha keto-adipic acid, alpha.-keto-caproic acid, alpha keto isovalerate, alpha ketoglutarate, and mixtures thereof, were not as effective as SRF in enhancing the synthesis, secretion and transport of adhesion molecules, collagen and elastin needed for enhanced wound strength, wound texture and pigmentation. SRF eliminated all the irritation and enhanced re-epithelization and wound strength of skin by over 40% over sodium pyruvate alone or in combination with other alpha keto acids and fatty acids, when formulated into skin lotions to treat various wounds including dermabrasion, cuts, scratches, lacerations, punctures, contusions, post laser wounds, surgery wounds, UV damage, sunburns, dry weather wounds, bacterial infection wounds, fungus infection wounds, virus infection wounds, irritant wounds, allergen wounds, and wounds from substances harmful micro wounds from dry skin. Even though other salts of pyruvic acid like calcium or potassium etc have been suggested, no one to date has evaluated the different salts individually or in combination for their ability to enhance wound healing. To evaluate the irritation or toxicity levels of these salts a formulation of each salt of pyruvate was tested against the standard formulations with sodium pyruvate that was shown to be non toxic in humans and animal studies. Potassium pyruvate, and calcium pyruvate, produced similar wound healing results in patients as the sodium pyruvate formulations. The zinc pyruvate, magnesium pyruvate, manganese pyruvate, aluminum pyruvate, ammonium pyruvate, and lithium pyruvate did produce slight increases in healing but did not achieve the results that sodium pyruvate produced, and they were irritating and possibly toxic. The combination of calcium pyruvate, magnesium pyruvate and L proline and citrulline was superior to all other combinations.

As used herein, the following terms have the given meanings:

The term "cytotoxicity", as used herein, means a condition caused by a cytotoxic agent that injures the cell. Injured cells do not readily proliferate because injured cells expend all energy on cellular repair. Aiding cellular repair promotes cellular proliferation.

The term "injured cell", as used herein, means a cell that has any cellular activity disrupted for any reason. For example, an injured cell may be a cell that has injured membranes or damaged DNA, RNA, and/or ribosomes. For example, a cell which has (a) injured membranes so that transport through the membranes is diminished resulting in an increase in toxins and normal cellular wastes inside the cell and a decrease in nutrients and other components necessary for cellular repair inside the cell (b) an increase in concentration of oxygen radicals inside the cell because of the decreased ability of the cell to produce antioxidants and enzymes, or (c) damaged DNA, RNA, and ribosomes which must be repaired or replaced before normal cellular functions can be resumed.

The term "metabolite, as used herein, refers to any substance produced by metabolism or by a metabolic process. "Metabolism," as used herein, refers to the various chemical reactions involved in the transformation of molecules or chemical compounds occurring in tissue and the cells therein.

The term "pharmaceutically acceptable", as used herein, such as pharmaceutically acceptable carrier, excipient, etc. means pharmacologically acceptable and substantially non-toxic to the subject to which the particular compound is administered.

The term "pharmaceutically acceptable salt", as used herein, refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hydroscopicity, flowability and solubility of compounds. See, e.g., H. Ansel et. al., Pharmaceutical Dosage Forms and Drug Delivery Systems (6th Ed. 1995) at pp. 196 and 1456-1457.

The term "prodrug", as used herein, refers to compounds, which undergo biotransformation prior to exhibiting their pharmacological effects. The chemical modification of drugs to overcome pharmaceutical problems has also been termed "drug latentiation." Drug latentiation is the chemical modification of a biologically active compound to form a new compound, which upon in vivo enzymatic attack will liberate the parent compound. The chemical alterations of the parent compound are such that the change in physicochemical properties will affect the absorption, distribution and enzymatic metabolism. The definition of drug latentiation has also been extended to include nonenzymatic regeneration of the parent compound. Regeneration takes place as a consequence of hydrolytic, dissociative, and other reactions not necessarily enzyme mediated. The terms prodrugs, latentiated drugs, and bioreversible derivatives are used interchangeably. By inference, latentiation implies a time lag element or time component involved in regenerating the bioactive parent molecule in vivo. The term prodrug is general in that it includes latentiated drug derivatives as well as those substances, which are converted after administration to the actual substance, which combines with receptors. The term prodrug is a generic term for agents, which undergo biotransformation prior to exhibiting their pharmacological actions.

The term "reactive oxygen species", as used herein, means activated oxygen species such as superoxide ($O_2^-$), hydrogen peroxide ($H_2O_2$), hydroxyl radicals (OH), and singlet oxygen ($^1O_2$). Preferably, the reactive oxygen species is superoxide and hydrogen peroxide. More preferably, the reactive oxygen species is hydrogen peroxide.

The term "resuscitation", as used herein, of injured mammalian cells means the reversal of Cytotoxicity, the stabilization of the cellular membrane, an increase in the proliferation rate of the cell, and/or the normalization of cellular functions such as the secretion of growth factors, hormones, wound strength, texture, elasticity and pigmentation and the like.

The term "therapeutically effective amount", as used herein, means an amount of at least one compound of the invention, or a pharmaceutically acceptable salt thereof, which is effective to prevent, alleviate or ameliorate symptoms of disease or prolong the survival of the subject being treated. Determination of a therapeutically effective amount is within the skill in the art.

The cells which may be treated with the therapeutic wound-healing compositions of the present invention are mammalian cells. Although the present therapeutic wound-healing compositions are useful for treating mammalian epidermal keratinocytes and mammalian monocytes, applicant contemplates that the therapeutic wound-healing compositions may also be used to protect or resuscitate all mammalian cells. Keratinocytes are representative of normal mammalian cells and are the fastest proliferating cells in the body. The correlation between the reaction of keratinocytes to injury and therapy and that of mammalian cells in general is very high. Monocytes are representative of specialized mammalian cells such as the white blood cell in the immune system and the organ cells in liver, kidney, heart, and brain. The mammalian cells may be treated in vivo and in vitro.

Epidermal keratinocytes are the specialized epithelial cells of the epidermis which synthesize keratin, a scleroprotein which is the principal constituent of epidermis, hair, nails, horny tissue, and the organic matrix of the enamel of teeth. Mammalian epidermal keratinocytes constitute about 95% of the epidermal cells and together with melanocytes form the binary system of the epidermis. In its various successive stages, epidermal keratinocytes are also known as basal cells, prickle cells, and granular cells.

Particular disease states to be treated in the invention include wrinkles, aging skin, cellulitis, wounds and diseases which are selected from the group consisting of infected and noninfected wounds, bacterial infections, fungal infections, viral infections, cold sores, thermal burns, sunburns, chemical burns, surgical wounds, psoriasis, eczema, decubitus ulcers, cancer, diabetic ulcers, dermatoses, inflammatory diseases, and wounds resulting from laser treatment, micro-wounded skins, scratches, micro-needling, abrasions, laceration, puncture, dry skin, contact with irritants, contact with allergens or other substances that are harmful to skin or skin cells and any type of wound resulting from laser treatments for the removal of scar and wrinkles, hair removal.

The pyruvates are magnesium pyruvate and calcium pyruvate. The total dosage of these two pyruvates may constitute about 0.10% to about 5.0%, based on total weight of the composition. Preferred is about 0.2% to about 4.0% and most preferred is about 0.5% to about 4.0%. The dosage of L proline may constitute about 0.1% to about 3.0%, based on total weight of the composition. Preferred is about 0.2% to about 2.5% and most preferred is about 0.5% to about 2.5%. For the citrulline (L citrulline, citrulline malate or combinations thereof) the ranges are the same as for L proline. While the ranges are the same, in any given specific formula, the amount of these two constituents may, and are likely, different from each other, e.g., 2% L proline and 1.3% citrulline. The term "liquid carrier" as used herein is meant to include any flowable material that will transport the present invention formulation with having detrimental effects thereon. These include water, oil, water-based carriers, oil-based carriers, gels, emulsions, lotions, creams, solutions and petrolatum. Preferred are oils, gels, lotions and petrolatum. As shown elsewhere herein the forgoing formulas may also include other actives without exceeding the scope of the invention. These would include other pyruvates, acids, and derivatives thereof, and/or antioxidants, antibacterial agents, and other actives, as described below.

There may be pyruvate precursors included that may be selected from the group consisting of pyruvyl-glycine, pyruvyl-alanine, pyruvyl-cysteine, pyruvyl-leucine, pyruvyl-valine, pyruvyl-isoleucine, pyruvyl-phenylalanine, pyruvamide, ethyl pyruvate and salts of pyruvic acid. The pyruvate in the present invention may be selected from the group consisting of pyruvic acid, pharmaceutically acceptable esters such as methyl, ethyl, and salts of pyruvic acid, prodrugs of pyruvic acid, and mixtures thereof.

The alpha-keto acids having four or more carbon atoms may be selected from the group consisting of oxaloacetic acid, alpha-keto-glutaric acid, alpha-keto-butyric acid, alpha-keto-adipic acid, .alpha.-keto-caproic acid, and .alpha.-keto-isovaleric acid. The precursors of .alpha.-keto acids having four or more carbon atoms may be selected from the group consisting of .alpha.-keto acid-glycine, .alpha.-keto acid-cysteine, .alpha.-keto acid-alanine, .alpha.-keto acid-leucine, .alpha.-keto acid-valine, .alpha.-keto acid-isoleucine, and .alpha.-keto acid-phenylalanine.

The amount of pyruvates or alpha keto acids in combination with SRF present in the therapeutic wound healing compositions of the present invention is a therapeutically effective amount. A therapeutically effective amount of pyruvates and alpha keto acids and SRF is that amount necessary for the inventive composition to prevent and reduce injury to mammalian cells and increase the synthesis of collagen, elastin, to increase wound strength texture and pigmentation. The exact amount of pyruvates or alpha keto acids and SRF is a matter of preference subject to such factors as the type of condition being treated as well as the other ingredients in the composition. In a preferred embodiment, pyruvates, or alpha keto acids in combination with SRF is present in the therapeutic wound healing composition in an amount from about 0.010% to about 5%. and more preferably from about 1% to about 3%, by weight.

In another preferred embodiment, the method may further comprise contacting the mammalian cells with SRF and a therapeutic agent. The therapeutic agent may be selected from the group consisting of antibacterials, antivirals, antifungals, antitumors, antihistamines, proteins, enzymes, hormones, nonsteroidal anti-inflammatories, cytokines, and steroids. The therapeutic agent may be administered prior to administration of SRF, or with the administration of SRF.

The amount of therapeutic agent present in the therapeutic compositions of the present invention is a therapeutically effective amount. A therapeutically effective amount of a therapeutic agent is the usual amount of therapeutic agent necessary to treat the particular condition. The exact amount of therapeutic agent is a matter of preference subject to such factors as the type of condition being treated as well as the other ingredients in the composition. In general, the amount of antibacterial agent present is the ordinary dosage required to obtain the desired result. Such dosages are known to the skilled practitioner in the medical arts and are not a part of the present invention.

The antibacterial agents which may be employed in the therapeutic compositions may be selected from a wide variety of water-soluble and water-insoluble drugs, and their acid addition or metallic salts, useful for treating infections. Both organic and inorganic salts may be used provided the antibacterial agent maintains its medicament value. The antibacterial agents may be selected from a wide range of therapeutic agents and mixtures of therapeutic agents which may be administered in sustained release or prolonged action form. Nonlimiting illustrative specific examples of antibacterial agents include bismuth containing compounds, sulfonamides; nitrofurans, metronidazole, tinidazole, nimorazole, benzoic acid; aminoglycosides, macrolides, penicillins, polypeptides, tetracyclines, cephalosporins, chloramphenicol, and clindamycin. Preferably, the antibacterial agent is selected from the group consisting of bismuth containing compounds, such as, without limitation, bismuth aluminate, bismuth subcitrate, bismuth subgalate, bismuth subsalicylate, and mixtures thereof; the sulfonamides; the nitrofurans, such as nitrofurazone, nitrofurantoin, and furozolidone; and miscellaneous antibacterials such as metronidazole, tinidazole, nimorazole, and benzoic acid; and antibiotics, including the aminoglycosides, such as gentamycin, neomycin, kanamycin, and streptomycin; the macrolides, such as erythromycin, clindamycin, and rifamycin; the penicillins, such as penicillin G, penicillin V, Ampicillin and amoxicillin; the polypeptides, such as bacitracin and polymyxin; the tetracyclines, such as tetracycline, chlorotetracycline, oxytetracycline, and doxycycline; the cephalosporins, such as cephalexin and cephalothin; and miscellaneous antibiotics, such as chloramphenicol, and clindamycin. More preferably, the antibacterial agent is selected from the group consisting of bismuth aluminate, bismuth subcitrate, bismuth subgalate, bismuth subsalicylate, sulfonamides, nitrofurazone, nitrofurantoin, furozolidone, metronidazole, tinidazole, nimorazole, benzoic acid, gentamycin, neomycin, kanamycin, streptomycin, erythromycin, clindamycin, rifamycin, penicillin G, penicillin V, Ampicillin amoxicillin, bacitracin, polymyxin, tetracycline, chlorotetracycline, oxytetracycline, doxycycline, cephalexin, cephalothin, chloramphenicol, clindamycin and Mupirocin.

The amount of antibacterial agent which may be employed in the therapeutic compositions of the present invention may vary depending upon the therapeutic dosage recommended or permitted for the particular antibacterial agent. In general, the amount of antibacterial agent present is the ordinary dosage required to obtain the desired result. Such dosages are known to the skilled practitioner in the medical arts and are not a part of the present invention. In a preferred embodiment, the antibacterial agent in the therapeutic composition is present in an amount from about 0.01% to about 10%, preferably from about 0.1% to about 5%, and more preferably from about 1% to about 3%, by weight.

The antiviral agents which may be employed in the therapeutic compositions may be selected from a wide variety of water-soluble and water-insoluble drugs, and their acid addition or metallic salts, useful for treating infections. Both organic and inorganic salts may be used provided the antiviral agent maintains its medicament value. The antiviral agents may be selected from a wide range of therapeutic agents and mixtures of therapeutic agents which may be administered in sustained release or prolonged action form. Nonlimiting illustrative categories of such antiviral agents include RNA synthesis inhibitors, protein synthesis inhibitors, immunostimulating agents, protease inhibitors, and cytokines. Nonlimiting illustrative specific examples of such antiviral agents include the following medicaments.
Preferred antiviral agents to be employed may be selected from the group consisting of acyclovir, Imiquimod, Foscarnet sodium, ribavirin, vidarabine, ganeiclovir sodium, zidovudine, phenol, amantadine hydrochloride, and interferon alpha.-n3. In a preferred embodiment, the antiviral agent is selected from the group consisting of acyclovir, foscarnet sodium, ribavirin, vidarabine, Remesivir, and ganeiclovir sodium. In a more preferred embodiment, the antiviral agent is acyclovir.

The amount of antiviral agent which may be employed in the therapeutic compositions of the present invention may vary depending upon the therapeutic dosage recommended or permitted for the particular antiviral agent. In general, the amount of antiviral agent present is the ordinary dosage required to obtain the desired result. Such dosages are known to the skilled practitioner in the medical arts and are not a part of the present invention. In a preferred embodiment, the antiviral agent in the therapeutic composition is present in an amount from about 0.1 to about 20%, preferably from about 1 to about 10%, and more preferably from about 2% to about 7%, by weight.

The antifungal agents which may be employed in the therapeutic compositions may be selected from a wide variety of water-soluble and water-insoluble drugs, and their acid addition or metallic salts, useful for treating fungal infections. Both organic and inorganic salts may be used provided the antifungal agent maintains its medicament value. The antifungal agents may be selected from a wide range of therapeutic agents and mixtures of therapeutic agents which may be administered in sustained release or prolonged action form. Nonlimiting illustrative specific examples of antifungal agents include the following medicaments: miconazole, clotrimazole, tioconazole, terconazole, povidone-iodine, and butoconazole. Other antifungal agents are lactic acid and sorbic acid. Preferred antifungal agents are miconazole and clotrimazole.

The amount of antifungal agent which may be employed in the therapeutic compositions of the present invention may vary depending upon the therapeutic dosage recommended or permitted for the particular antifungal agent. In general, the amount of antifungal agent present is the ordinary dosage required to obtain the desired result. Such dosages are known to the skilled practitioner in the medical arts and are not a part of the present invention. In a preferred embodiment, the antifungal agent in the therapeutic composition is present in an amount from about 0.05% to about 10%, preferably from about 0.1% to about 5%, and more preferably from about 0.2% to about 4%, by weight.

The antitumor agents which may be employed in the therapeutic compositions may be selected from a wide variety of water-soluble and water-insoluble drugs, and their acid addition or metallic salts, useful for treating cancers. Both organic and inorganic salts may be used provided the antitumor agent maintains its medicament value. The antitumor agents may be selected from a wide range of therapeutic agents and mixtures of therapeutic agents which may be administered in sustained release or prolonged action form. Nonlimiting illustrative specific examples include anti-metabolites, antibiotics, plant products, hormones, and other miscellaneous chemotherapeutic agents. Chemically reactive drugs having nonspecific action include alkylating agents and N-alkyl-N-nitroso compounds. Examples of alkylating agents include nitrogen mustards, aziridines (ethylenimines), sulfonic acid esters, and epoxides. Anti-metabolites are compounds that interfere with the formation or utilization of a normal cellular metabolite and include amino acid antagonists, 3, bromopyruvate, vitamin and coenzyme antagonists, and antagonists of metabolites involved in nucleic acid synthesis such as glutamine antagonists, folic acid antagonists, pyrimidine antagonists, and purine antagonists.

Antibiotics are compounds produced by microorganisms that have the ability to inhibit the growth of other organisms and include actinomycins and related antibiotics, glutarimide antibiotics, sarkomycin, fumagillin, streptonigrin, tenuazonic acid, actinogan, peptinogan, and anthracyclic antibiotics such as doxorubicin. Plant products include coichicine, podophyllotoxin, and vinca alkaloids. Hormones include those steroids used in breast and prostate cancer and corticosteroids used in leukemias and lymphomas. Other miscellaneous chemotherapeutic agents include urethan, hydroxyurea, and related compounds; thiosemicarbazones and related compounds; phthalanilide and related compounds; and triazenes and hydrazines, 2-Deoxy-D-glucose, Dichloroacetic acid, often abbreviated DCA, is the chemical compound with formula $CHCl_2COOH$. It is an acid, an analogue of acetic acid, Bromopyruvic acid, or bromopyruvate, is a synthetic brominated derivative of pyruvic acid. The anticancer agent may also be a monoclonal antibody or the use of X-rays. In a preferred embodiment, the anticancer agent is an antibiotic. In a more preferred embodiment, the anticancer agent is doxorubicin. In a most preferred embodiment, the anticancer agent is doxorubicin.

Antioxidants are substances which inhibit oxidation or suppress reactions promoted by oxygen or peroxides. Antioxidants, especially lipid-soluble antioxidants, can be absorbed into the cellular membrane to neutralize oxygen radicals and thereby protect the membrane. The antioxidants useful in the present invention may be selected from the group consisting of all forms of vitamin A (retinol), all forms of vitamin B (3,4-didehydroretinol), all forms of carotene such as .alpha.-carotene, .beta.-carotene, gamma-carotene, .sigma.-carotene, all forms of vitamin C (D-ascorbic acid, L-ascorbic acid), all forms of tocopherol such as vitamin E (.alpha.-tocopherol, 3,4-dihydro-2,5,7,8-tetramethyl-2-(4,8,12-trimethyltri-decyl)-2H-1-benzop-yran-6-ol), (alpha.-tocopherol, gamma-tocopherol, delta-tocopherol, tocoquinone, tocotrienol, and vitamin E esters which readily undergo hydrolysis to vitamin E such as vitamin E acetate and vitamin E succinate, and pharmaceutically acceptable vitamin E salts such as vitamin E phosphate, pro-drugs of vitamin A, carotene, vitamin C, and vitamin E, pharmaceutically acceptable salts of vitamin A, carotene, vitamin C, .alpha.-lipoic acid and vitamin E, and the like, and mixtures thereof. Preferably, the antioxidant is selected from the group of lipid-soluble antioxidants consisting of vitamin A, (carotene, vitamin E, vitamin E acetate, N-acetylcysteine and mixtures thereof. More preferably, the antioxidant is vitamin E or vitamin E acetate. Most preferably, the antioxidant is vitamin E acetate.

The amount of antioxidant present in the therapeutic wound-healing compositions of the present invention is also that which is a therapeutically effective amount. A therapeutically effective amount of antioxidant is that amount of antioxidant necessary for the inventive composition to prevent and reduce injury to mammalian cells or increase the resuscitation rate of injured mammalian cells. The exact amount of antioxidant is a matter of preference subject to such factors as the type of condition being treated as well as the other ingredients in the composition. In a preferred embodiment, the antioxidant is present in the therapeutic wound-healing composition in an amount from about 0.1% to about 40%, preferably from about 0.2% to about 30%, and more preferably from about 0.5% to about 20%, by weight of the therapeutic wound-healing composition.

The mixture of saturated and unsaturated fatty acids in the present invention are those fatty acids required for the repair of mammalian cellular membranes and the production of new cells. Fatty acids are carboxylic acid compounds found in animal and vegetable fat and oil. Fatty acids are classified as lipids and are composed of chains of alkyl groups containing from 4 to 22 carbon atoms, 0-3 double bonds and characterized by a terminal carboxyl group, —COOH. Fatty acids may be saturated or unsaturated and may be solid, semisolid, or liquid. The most common saturated fatty acids are butyric acid (C4), lauric acid (C12), palmitic acid (C16), and stearic acid (C18). Unsaturated fatty acids are usually derived from vegetables and consist of alkyl chains containing from 16 to 22 carbon atoms and 0-3 double bonds with the characteristic terminal carboxyl group. The most common unsaturated fatty acids are oleic acid, linoleic acid, and linolenic acid (all C18 acids).

In a preferred embodiment, the mixture of saturated and unsaturated fatty acids has a composition similar to that of human fat and comprises the following fatty acids: butyric acid, caproic acid, caprylic acid, capric acid, lauric acid, myristic acid, myristoleic acid, palmitic acid, palmitoleic acid, stearic acid, oleic acid, linoleic acid, linolenic acid, arachidic acid, and gadoleic acid. Preferably, butyric acid, caproic acid, caprylic acid, capric acid, lauric acid, myristic acid, myristoleic acid, palmitic acid, palmitoleic acid, stearic acid, oleic acid, linoleic acid, linolenic acid, arachidic acid, and gadoleic acid are present in the mixture in about the following percentages by weight, respectively (carbon chain number and number of unsaturation's are shown parenthetically, respectively): 0.2%-0.4% (C4), 0.1% (C6), 0.3%-0.8% (C8), 2.2%-3.5% (C10), 0.9%-5.5% (C12), 2.8%-8.5% (C14), 0.1%-0.6% (C14:1), 23.2%-24.6% (C16), 1.8%-3.0% (C16:1), 6.9%-9.9% (C18), 36.0%-36.5% (C18:1), 20%-20.6% (C18:2), 7.5%-7.8% (C18:3), 1.1%-4.9% (C20), and 3.3%-6.4% (C20:1).

In another preferred embodiment, the mixture of saturated and unsaturated fatty acids comprises lecithin. Lecithin (phosphatidylcholine) is a phosphatide found in all living organisms (plants and animals) and is a significant constituent of nervous tissue and brain substance. Lecithin is a mixture of the diglycerides of stearic, palmitic, and oleic acids, linked to the choline ester of phosphoric acid. The product of commerce is predominantly soybean lecithin obtained as a by-product in the manufacturing of soybean oil. Soybean Lecithin contains palmitic acid 11.7%, stearic 4.0%, palmitoleic 8.6%, oleic 9.8%, linoleic 55.0%, linolenic 4.0%, C20 to C22 acids (includes arachidonic) 5.5%. Lecithin may be represented by the formula: $CH_2OCOR$—$CHOCOR$—$CH_2O$—$P(O)$—$OCH_2CH_2N+(CH_3-)_3$, wherein R is selected from the group consisting of stearic, palmitic, avocado oil and oleic acid.

The above fatty acids and percentages thereof present in the fatty acid mixture are given as an example. The exact type of fatty acid present in the fatty acid mixture and the exact amount of fatty acid employed in the fatty acid mixture may be varied in order to obtain the result desired in the final product and such variations are now within the capabilities of those skilled in the art without the need for undue experimentation.

The amount of fatty acids present in the therapeutic wound-healing compositions of the present invention is a therapeutically effective amount. A therapeutically effective amount of fatty acids is that amount of fatty acids necessary to prevent and reduce injury to mammalian cells or increase the resuscitation rate of injured mammalian cells. The exact amount of fatty acids employed is subject to such factors as the type and distribution of fatty acids employed in the mixture, the type of condition being treated, and the other ingredients in the composition. In a preferred embodiment, the fatty acids are present in the therapeutic wound-healing composition in an amount from about 1.0% to about 50%, preferably from about 2.0% to about 45%, and more preferably from about 2.5% to about 40%, by weight of the therapeutic wound-healing composition.

EXAMPLES

The purpose of the examples below was to demonstrate efficacy of (SRF) to repair and enhance cellular transport systems to enhance the synthesis, secretion and transport of adhesion molecules, skin phospholipids and type 1 collagen to increase wound strength, wound texture, and pigmentation in wounds and treat wrinkles. All other formulas to date without SRF, enhanced the rate of healing, but did not increase wound strength, texture or pigmentation. When the SRF formula was used, it produced superior wound healing results. Magnesium pyruvate and calcium pyruvate are needed by enzyme systems to increase the synthesis of adhesion molecules and melanin. L proline increased collagen synthesis and L-Citrulline increased the local production of nitric oxide that increased vacuolization to enhance the rate of healing. In combination they demonstrated a synergistic effect that increased wound strength, texture and pigmentation over the individual components.

Example 1 Rat Wound Strength Healing Studies

SRF with and without antioxidants and fatty acids, administered topically, reversed impaired wound healing and increased wound strength by doxorubicin (Doxo) and other cancer or AIDS drugs in rats. Other cancer or HIV drugs tested that have been shown to impair wound healing and decrease wound strength included bleomycin, cisplatin, Urushiol, Imiquimod, Carboplatin, floxuridine, methotrexate, oxaliplatin, Bevacizumab, radiation, and the AIDS drugs including: Nucleoside Reverse Transcriptase Inhibitors (NRTI), Fusion Inhibitors, Highly Active Antiretroviral Therapy (HAART), and Non-Nucleoside Reverse Transcriptase Inhibitors (NNRTI).

Rats given Doxo (6 mg/kg i.v.) were wounded with linear dermal incisions, and the wound-breaking strength (WBS) was compared among groups of rats differently treated with SRF (calcium pyruvate, magnesium pyruvate, L proline and citrulline) with and without antioxidants and fatty acids. Wound breaking strength is a measurement of wound strength after injury compared to normal noninjuried skin. Fourteen groups of five rats each were studied. The SRF was administered topically daily. All groups were wounded at postoperative day 0, at which time Doxo was given to all Groups. All wounds were harvested at POD 21, and the mean wound breaking strength (WBS) of each group was obtained using an Instron Tensiometer. Doxorubicin impaired normal wound strength by 40 percent. Topical administration of SRF formulas restored WBS in Doxo-treated rats to 86 percent of control values. In conclusion, SRF was shown to restore wound strength, and texture which demonstrates the increased synthesis and transport of collagen, cardiolipin, phospholipids and elastin and pigmentation to nearly normal levels in doxorubicin-impaired wounds.

See Table I:

TABLE I

Testing The Various Topical Wound Healing Formulas For Wound Breaking Strength And Texture And Pigmentation Without And With SRF, Or With Or Without Certain SRF Components (2% Calcium And 2% Magnesium Pyruvate, 1% L Proline And 1% L-Citrulline) In The Topical Vehicles In Doxorubicin Treated Wounded Hairless Rats Compared To Non-Wounded Normal Skin.

| Formula | Days to healing | Percentage of wound breaking strength, by day 21 |
|---|---|---|
| Normal non wounded skin | 0 | 100% |
| Untreated control | 18 | 40% |
| Vehicle Petrolatum | 16 | 48% |
| Calcium pyruvate without L proline Or L-citrulline | 14 | 42% |
| Calcium pyruvate with L proline | 16 | 44% |
| Calcium pyruvate with L-citrulline | 16 | 51% |
| Calcium pyruvate with L proline And L-citrulline | 13 | 54% |
| Magnesium pyruvate without L proline Or L-citrulline | 14 | 44% |
| Magnesium pyruvate with L proline | 15 | 42% |
| Magnesium pyruvate with L-citrulline | 16 | 55% |
| Magnesium pyruvate with L proline And L-citrulline | 13 | 58% |
| Magnesium pyruvate and Calcium pyruvate without L proline Or L-citrulline | 16 | 48% |
| Calcium pyruvate and Magnesium pyruvate alone With L-citrulline | 13 | 52% |
| Calcium pyruvate and Magnesium pyruvate with L Proline But without L-citrulline | 15 | 42% |
| Calcium pyruvate and Magnesium pyruvate with Proline And with L-citrulline (SRF) | 11 | 88% |
| Neosporin without SRF Commercial formula | 15 | 51% |
| Neosporin commercial formula, with SRF | 11 | 86% |

All cancer drugs inhibit and damage mitochondria and impair wound healing after treatment with chemotherapy or radiation. 1.6 days faster healing or greater than 10% over the vehicle control is considered statistically significant by the FDA. Also, a 10% increase in wound strength is considered clinically and statistically significant by the FDA. Analysis of the biopsies showed a greater increase in collagen type I, over type II or type III with SRF. Type I is associated with wound strength. This experiment clearly showed that the addition of SRF reversed the negative effects of cancer drugs and enhanced the healing process over other formula.

Example 2

All previous studies using pyruvate to treat wounds or be used as an antioxidant used only the sodium salt form of pyruvic acid. The drug products that were tested in previous studies used 1-3% sodium pyruvate and other sodium salts of alpha keto acids by weight 1-3% concentrations in the lotions and triple antibiotic formulations. Even though other salts of pyruvic acid like calcium or magnesium etc. have been suggested, no one to date has evaluated the different salts individually or in combination for their ability to enhance cellular repair, mitochondrial repair, enhanced synthesis of adhesion molecules and collagen, to increase wound strength, texture and pigmentation, or to reduce irritation. Blood levels of the various salts mg/liter are 3220 mg for Sodium, 200 mg for potassium, 27 mg for magnesium, 70 mg for calcium, 1.1 mg for zinc, 0.02 mg for manganese, 6 mg for lithium, 0.03 mg for aluminum, 0.06 mg for ammonium and 0.36 mg for phosphorus. To evaluate the irritation or toxicity levels of these salt formulations, each salts of pyruvate (sodium, calcium, magnesium, potassium, zinc, manganese, lithium and ammonium were tested. Using the same concentrations of pyruvate of for each salt on skin laser wounds in patients, the use of potassium pyruvate, magnesium pyruvate, calcium pyruvate, zinc pyruvate, manganese pyruvate, lithium pyruvate, aluminum pyruvate, and ammonium pyruvate were tried. Potassium pyruvate, and calcium pyruvate, produced similar wound healing results in patients as the sodium pyruvate formulations. The zinc pyruvate, magnesium pyruvate, manganese pyruvate, aluminum pyruvate, ammonium pyruvate, and lithium pyruvate did not produce increases in healing over the base and did not increase wound strength, texture or pigmentation to achieve the results that SRF produced, and they were irritating and possibly toxic producing skin irritation. When irritation and healing was measured against formulas that contained Sodium pyruvate only, only SRF was superior in reducing irritation from drugs by over 20%, decreasing healing times by 25% and increasing wound strength by 45% which is considered clinically significant by the FDA. Table I The amount of the salts delivered in the formulations with pyruvates were compared to the amounts of the salts in human blood. The salts of pyruvic acid or pyruvate, sodium, potassium, and calcium, were all under amounts found in human blood. The delivered salts of pyruvic acid or pyruvate like including zinc in this formulation was 840× blood levels, the magnesium was 40× blood levels, the manganese was 3,700× blood levels, aluminum was 6100× times blood levels, the ammonium was 533× times blood levels, and lithium was 50× blood levels. The use of these salts of pyruvic acid at these levels proved, that one cannot assume that all the salts of pyruvate are non-irritating. Even though the use of the sodium salt of pyruvic acid showed no irritation on dermabraided skin, and enhanced healing, the others did produce irritation and the use of some of these salts over time would have a negative effect on healing. The sodium salt of pyruvate used was 59 times lower than sodium in blood, the calcium was 1.5× times lower, and the potassium was 3.2× times lower than blood levels, thus they were well within the safe levels needed to deliver the pyruvate.

See Table II

TABLE II

Comparison Of Various Drugs Administered On Wounds With Or Without Sodium Pyruvate Or SRF (2% Calcium & 2% Magnesium Pyruvate, 1% L Proline And 1% L-Citrulline). Rating was 1-10, with 1 having the most amount of erythema and 10 having no erythema. Wound healing was also measured in days to total re-epithelization.

| Various Drugs | Drugs in commercial formula erythema | Drugs in commercial formula with sodium pyruvate only erythema | in Drugs commercial formula with SRF erythema | Drug in commercial formula Days to healing | Drug in commercial formula with sodium pyruvate only. Days to healing | in Drug commercial formula with SRF. Days to healing |
|---|---|---|---|---|---|---|
| Mupirocin | 4 | 6 | 8 | 20 | 15 | 11 |
| Neosporin | 5 | 5 | 6 | 20 | 13 | 11 |
| erythromycin | 6 | 5 | 8 | 19 | 13 | 9 |
| mafenide | 8 | 8 | 7 | 18 | 14 | 12 |
| Acyclovir | 4 | 5 | 7 | 18 | 13 | 10 |
| Famciclovir | 5 | 6 | 7 | 17 | 14 | 12 |
| valaciclovir | 8 | 8 | 8 | 18 | 17 | 14 |
| Penciclovir | 7 | 7 | 8 | 17 | 16 | 12 |
| Chlotrimizole | 4 | 6 | 8 | 22 | 15 | 11 |
| butenafine | 3 | 4 | 5 | 21 | 18 | 16 |
| naftifine | 3 | 6 | 7 | 20 | 14 | 13 |
| econazole | 6 | 6 | 6 | 19 | 17 | 14 |
| ketoconazole | 3 | 6 | 8 | 23 | 20 | 14 |
| microazole | 5 | 6 | 7 | 19 | 12 | 11 |
| oxiconazole | 6 | 7 | 9 | 18 | 14 | 11 |
| tolnaftate | 7 | 7 | 7 | 21 | 13 | 10 |
| sulconazole | 4 | 6 | 8 | 20 | 15 | 11 |
| ciclopirox | 4 | 5 | 9 | 20 | 11 | 9 |
| nystatin | 2 | 6 | 8 | 17 | 14 | 12 |
| Retinol | 1 | 3 | 7 | 19 | 15 | 9 |
| Averages | 4.6 | 5.4 | 7.05 | 18.5 | 16.05 | 11.6 |

The results clearly show that SRF was superior in reducing erythema by 24% and decreasing healing time over sodium pyruvate by 38% which is clinically significant.

Example 3 C-14 Testing

In rat tissue culture studies, using C 14 labeled calcium and magnesium pyruvate C 14 labeled L-Proline and L-citrulline (SRF); tissue culture analysis clearly showed that SRF increased the production of collagen by 60% over the non SRF formulas which only caused a 20% increase. All the individual 14c labeled components including calcium and magnesium pyruvate, L-proline, and L-citrulline only increased collagen by 10-18%. Incorporation of [U-(14)C] L proline into total collagen increased 19-53% over the 2-hr with medium containing SRF. It was also discovered that 30% of the radioactive calcium or magnesium pyruvate was incorporated into phosphatidylcholine the main membrane cellular lipid (fatty acid), and 10% into elastin, when calcium pyruvate, magnesium pyruvate with L proline and citrulline, were present (SRF). In short, calcium and magnesium are needed by the enzyme systems to synthesize and transport cellular membrane components, and the addition of L proline increased the synthesis of collagen. The use of the SRF formulation was synergistic and produced the best healing results of all previous combinations of alpha keto acids tested to date and eliminated the need to provide fatty acids from olive oil, cottonseed oil and cocoa butter.

Example 4 SRF Formulation

Topical formula: To one liter of lotion or gel vehicle or petrolatum, add 0.7% (7.0 grams) to 3% (30 grams) of calcium pyruvate, 1 gram or 0.1% to 2% of magnesium pyruvate and 0.1 to 1% of L proline or and 0.1 to 1.0% L-citrulline. This formula has many modifications to deliver the correct amount of calcium or magnesium pyruvate, L proline and L-citrulline. Calcium can be delivered as calcium pyruvate, with or without the addition of calcium chloride, calcium carbonate, calcium acetate, calcium citrate, calcium lactate, and calcium sulfate. Magnesium can be delivers as magnesium pyruvate, with and without the addition of magnesium chloride, magnesium phosphate, magnesium bicarbonate. L proline is L-proline and citrulline as L-citrulline or citrulline malate. The PH should be adjusted to 6.4 with sodium hydroxide. Pyruvate provides the energy to synthesize membrane phospholipids, collagen elastin and increase wound strength and texture. Calcium and magnesium are needed for enzymes to make elastin and collagen. Magnesium is also needed for mitochondrial membrane stability, for the production of ATP and to increase wound strength and texture and pigmentation. L-proline increases the synthesis and transport of collagen to increase wound strength and citrulline increases nitric oxide at the site to increase blood flow.

Example 4

The purpose of the study was to confirm the effects of alpha-keto acid alone or in combinations for their effects on the rate of cutaneous healing and wound breaking strength on 20 patients. The combinations were pyruvate and keto isovalerate and pyruvate with alpha keto glutarate were tested with and without SRF. The wound model utilized an arm design wherein the wound was created by a well defined model of laser skin resurfacing a wound that is very similar to a bad sunburn. 20 patients were tested with various formula. Four laser wounds were made on each subject's arm and the subjects were used as their own control. This model utilized pulsed $CO_2$ and Er: YAG lasers in a defined protocol (computerized scanner for $CO_2$ and uniform pulses with Er: YAG) which removes the entire stratum. Patient diaries were maintained to assess erythema, crusting, pain, itching, swelling, pigmentary changes, and the day of first make-up application. Blinded objective grading of improvement was independently assessed by 4 blinded observers at time intervals 3, 6, and 10 days, and 1, 2, and 4 months. Chromometer measurements of erythema were also analyzed and percentage moisture recorded.

Current laser skin resurfacing techniques averages 5-7 days to skin re-epithelialization (healing) whereas a few years ago, 10-14 days was typical. For ethical reasons, the selected the current "standard of care" model and thus the "delta value" for wound-healing between active and control should be greater/more significant for other types of wounds. All laser wounds remain red for weeks to months, due to inflammation and the over production of peroxynitrite. The study design did not address the final redness issue in the diaries, but rather utilized a Minolta Chromometer to look at relative values of erythema. The "LAB" color space model was used wherein the "A" value correlates with erythema. Reepithialization is the epithelial skin cells covering the entire wound. Visual appearance is determined by how many days it takes a wound to return to a normal appearance in terms of color (reduced redness) pigmentation, and texture wound strength.

See Table III and Table IV

TABLE III

Post Laser Healing Results. Re-Epithelization with Various Formulations All in A Gel Based Vehicle Delivered in Strips That Were Applied to One Of The Eight Sites on An Arm Daily for Two Weeks. Pyruvate Is Sodium Pyruvate and SRF Contains 2% Calcium and 2% Magnesium Pyruvate, 1% L Proline And 1% L-Citrulline

| Formula | Days to healing 100% reepithelization | Days to normal appearance | percent healing over vehicle control |
|---|---|---|---|
| untreated control | 26 | 38 | — |
| Gel lotion vehicle control | 22 | 28 | 0% |
| Pyruvate & Ketoisovalerate Without SRF | 19 | 22 | 24% |
| Pyruvate & ketoglutarate Without SRF | 20 | 24 | 22% |
| Pyruvate & Ketoisovalerate And alpha ketoglutarate Without SRF | 18 | 20 | 23% |
| SRF formula | 15 | 14 | 56% |
| Pyruvate & ketoglutarate With SRF formula | 15 | 15 | 59% |
| Pyruvate & ketoglutarate & keto isovalerate in SRF formula | 11 | 14 | 57% |

1.6 days faster healing or greater than 10% over the vehicle control is considered statistically significant by the FDA.

TABLE IV

Post Laser Healing Results, Re-Epithelization With Various Formulations. Testing Of Formulas Containing Sodium Pyruvate (Pyruvate) Other Keto Acids With And Without Skin Resuscitation Factor (SRF) In A Petrolatum Base.

| Formula | Days to healing | Days to normal Appearance | percent healing over vehicle control |
|---|---|---|---|
| Untreated control | 26 | 38 | — |
| Aquaphor | 22 | 29 | 0 |
| Neosporin with sodium Pyruvate, vitamin E and fatty acids | 16 | 24 | 26% |
| Pyruvate & Ketoisovalerate | 15 | 21 | 22% |
| Pyruvate & ketoglutarate | 15 | 21 | 24% |
| Pyruvate & ketoglutarate Vitamin E and Fatty acids | 14 | 20 | 32% |
| Pyruvate & keto isovalerate Vitamin E And fatty acids | 13 | 19 | 33% |
| Sodium pyruvate, Ketoglutarate Vitamin E Fatty Acids and SRF | 12 | 18 | 76% |
| SRF | 12 | 18 | 74% |
| Sodium Pyruvate, vitamin E and fatty acids in SRF formula | 11 | 18 | 78% |

1.6 days faster healing or greater than 10% over the vehicle control is considered statistically significant by the FDA.

These experiments clearly showed that, SRF enhanced healing by increasing the synthesis of cellular phospholipids, cellular adhesions molecules, collagen, and increased wound healing, wound strength, texture and pigmentation over all other formulas. The SRF formula was also tested one hour after a total face laser resurfacing treatment. The right side of the face was treated with a cooling gel strip containing SRF to determine if the gel strip with SRF could reduce erythema, pain redness and increase the rate of healing over a non SRF treated site. The left side of the face was treated with the gel strip without SRF. Two hours after treatment, the right side treated with SRF produced a dramatic reduction in pain, redness, swelling and increased cooling. The left side of the face treated with the gel strip without SRF did not reduce redness, pain, and swelling. Monitoring the effects of SRF at the end of a week demonstrated that SRF produced better textured skin and pigmentation tones. Over a three week course the patients skin resolved and returned to normal in all places. The gel strip contained 2% SRF by weight.

Example 6 Post Laser Treatment (4 Subjects)

The purpose of this double blinded clinical study was to evaluate if the addition of Skin Resuscitation Factor (SRF)™ technology would positively affect wound healing of two (2) test products; 1) commercially available Abreva cream (docosonal) and 2) a commercially available triple antibiotic petrolatum-based ointment. The control products used in the study for comparison purposes were identical to the commercial products except they did not contain SRF.

Four laser wounds were made on each subject's arm and the subjects were used as their own control. Although the study population was small, the addition of SRF™ to both formulations accelerated the re-epithelialization of the subjects' skin. The relative increase among the subjects was a range of 10-60% at day 8 with some benefit evident at the remaining days until re-epithelialization had occurred. These percentages are statistically and clinically significant* values based on the requirements for enhanced healing claims. (* Based per FDA, which requires at least a 10% or approximately 1 day faster healing). This experiment showed that these formulae healed laser treated skin.

Example 7 (15 Subjects) Cold Sores

A commercial cold sore formula was purchased and the enumerated keto acids were placed into it to treat cold sores, both as a combination and singly as well. The commercial formulation by itself was utilized as a control. The normal cold sore formulas with phenol, an antiviral agent, did not work very well. However, when SRF was placed in the cold sore formulation both with and without anti-oxidants and fatty acids, they heal the cold sore at a much faster rate 10-40% when tested on a cold sore sufferer The same experiment was done with virally infected cells and the combination of pyruvate and α-Ketoisovalerate with SRF decreased viral plaque formation by 50%. Viral plaques are a direct measure of viral numbers in infected cells. The antiviral drug, Acyclovir also decreased viral plaques by 60% and SRF in combination with acyclovir, totally eliminated the virus from the infected cells. Other antiviral agents like docosonal produced better efficacy with the addition of SRF. Other antivirals were evaluated with SRF to determine if the addition of SRF could reduce the skin irritation produced by Foscarnet sodium, Ribavirin, imiquimod, vidarabine, ganciclovir sodium, zidovudine, phenol, amantadine hydrochloride, and interferon. alpha.-n3. Even though some of these anti virals are not effective against a cold sore, they were evaluated on human cold sores to determine if SRF could reduce the irritation and enhance healing at the infection site. All formula with SRF healed cold sore two days faster than non-treatments and when this formula was combined with antiviral, like acyclovir or docosonal, the viral lesions healed 1.5 days faster than the commercial antiviral agent alone (Abreva or acyclovir). The patients rated all the SRF antiviral formulations higher than the formulations containing the anti virals alone. On a 1-10 scale with 1 being far worse irritating than the formulation without SRF and 5 being equal and 10 being the least irritating most of the SRF formulations received a 7-8 compared to the formulations with only the antivirals (4-5 rating). The use of SRF formula with the addition of 0.1% Zinc lysine formula, produced the best lesion healing results.

Example 8 Anti-Wrinkle, Stretch Marks and Scar Removal and Prevention in Acne Tissue Culture Analysis of Collagen Production with SRF and Alpha Ketoglutarate Acid Alpha-ketoglutarate SRF formula worked synergistically to stimulated procollagen production in cultured human dermal fibroblasts, and decreases UVB-induced wrinkle formation in humans. The single salt of sodium alpha ketoglutarate or in combination with sodium pyruvate, was not as effective. Alpha-ketoglutarate is a key intermediate in the Krebs cycle, and a rate-limiting cofactor of prolyl-4-hydroxylase. It also has a potent effect on increasing the proline pool during collagen production. To investigate the effects of alpha-ketoglutarate on procollagen production and wrinkle formation, we conducted experiments in cultured human dermal fibroblasts and UVB-irradiated hairless mice. Based on ELISA measurements, alpha-ketoglutarate (10 microM) stimulated procollagen production in fibroblasts by 25.6+/−4.6% compared to vehicle (dH(2)O)-treated control cells. Also, we demonstrated that alpha-ketoglutarate increased activities of prolidase, which is known to play an important role in collagen metabolism, in fibroblasts and N-benzyloxycarbonyl-L-proline (Cbz-Pro), prolidase inhibitor, inhibited procollagen synthesis by alpha-ketoglutarate in fibroblasts. To determine the effect of topically applied alpha-ketoglutarate on wrinkle formation, alpha-ketoglutarate (1%) and vehicle (70% propylene glycol, 30% ethanol) were applied on the skin of UVB-induced patients 6 weeks. We found that alpha-ketoglutarate decreased wrinkle formation upon long-term topical application, but was irritating. These results suggest that alpha-ketoglutarate diminishes UVB-induced wrinkle formation by increasing collagen production, through a pathway that involves prolidase activation. Therefore, application of alpha-ketoglutarate may represent an effective anti-wrinkle agent for the cosmetic field. For example, alpha-keto glutarate reacts with hydrogen peroxide to form succinic acid which increases the production of hydrogen peroxide. Thus, when used alone as the sodium salt, with vitamin E and fatty acids, it is irritating and can injure cells and mitochondria and increase the damage to cellular membranes and inhibit the synthesis of collagen, elastin and decrease cellular longevity. Its use in this manner has been shown to delay healing and is irritating. Alpha keto glutarate in combination with SRF enhanced collagen deposition and wound strength with no skin irritation.

Skin application of SRF to remove wrinkles and firm skin with Collagen induction therapy (CIT) also known as microneedling RF or skin needling is a cosmetic procedure that involves repeatedly puncturing the skin with tiny, sterile needles (microneedling the skin). CIT should be separated from other contexts in which microneedling devices are used on the skin, e.g. transdermal drug delivery, vaccination. It is a technique for which research is ongoing but has been used for a number of skin problems including scarring and acne. Platelet-rich plasma (PRP) can be combined with collagen induction therapy treatment to enhance results. PRP is derived from the patient's own blood and contains many growth factors that increase collagen production. It can be applied topically to the entire treatment area during and after collagen induction therapy treatments and/or injected intradermally to scars. The use of microneedling followed by the application of SRF increased collagen deposition 78% more than microneedled skin alone. It also was used on turkey necks and wrinkles.

Example 9 Retinol Clinical Evaluation

In this randomized, parallel, double-blind, controlled clinical study, women applied to the entire face for 3 months in the morning and in the evening either the Retinol 0.2% cream or Retinol 0.2% cream with SRF (2% of calcium pyruvate, 2% of magnesium pyruvate, 1% of L proline, and 1% of L citrulline). Clinical and instrumental parameters were assessed at days 0, 4, 28, 56, and 84. Subject perception of the efficacy, tolerance of the tested products was assessed at days 1, 4, 10, 28, 56, and 84. A total of 34 women were enrolled, 17 that used the Retinol 0.2% cream and 17 that used the retinol 0.2% cream with SRF. Both products improved wrinkles, mottled pigmentation, pores, and global photodamage. A statistically significant differences was noted between Retinol 0.2% cream and Retinol 0.2% SRF cream. Adverse effects were mostly graded mild. Overall, Retinol 0.2%/with SRF cream was better tolerated than Retinol 0.2% cream without SRF. The Retinol cream without SRF was associated with a certain number of adverse effects (pruritus, burning sensation, erythema, and desquamation) currently known as "retinoid reaction". These adverse effects were totally eliminated when retinol was combined with SRF.

Clinical efficacy evaluations of wrinkles (frontal and glabellar area, eyes area, nasolabial fold), pores, and pigmentation were performed by a dermatologist using the photo numeric scales for aged skin before the first product application on Day 0 (baseline) and then on Day 4, Day 10, Day 28, Day 56, and Day 84. The Dermascore was used to assess, at all study visits, changes in pores and pigmentation. The Dermascore device is a modified dermatoscope equipped with appropriate polarizing filters. The color aspect alone is observed by removing the specular component with a cross-polarized analyzer, whereas the pore visibility is strengthened by increasing the proportion of specular reflexion with a parallel polarized analyzer. Mean values of roughness, depth, and texture were calculated from parameters measured along 16 lines around a defined point of the area to be evaluated. Subjects remained for at least 30 min prior and during instrumental measurements in a room with controlled temperature (20° C.±2° C.) and a relative humidity of 50%±5%. A decrease of values indicated an improvement of the skin relief.

Clinical Assessments

After 4 days of treatment with Retinol with SRF, a statistically significant improvement over retinol treatment without SRF was observed for wrinkles (P<0.001) nasolabial fold (p<0.001), and pigmentation (P<0.005) These differences were sustained from Day 5 onwards for wrinkles and from Day 8 onwards for pores and pigmentation. Improvement of horizontal wrinkles on the forehead and crow's feet was statistically significant over the Retinol cream with out SRF. A significant improvement was observed with Retinol 0.2% with SRF for the roughness, depth and texture as early as Day 8 vs day 28 for the Retinol cream without SRF.

Example 10 Post Laser Treatment (37 Subjects) for Tattoo and Hair Removal

SRF applied in a gel on post laser treatments for hair or tattoo removal decreased the irritation form the laser treatment and increased the healing time form 16 days to 10 days.

Example 11 Treatment of Infected Wounds

In this experiment a triple antibiotic formulation with SRF was used to treat skin infections and compared to a standard triple antibiotic without SRF in five patients. The patients had multiple infection sites and each site was treated with one of the two formulations. In all cases the infections resolved and were eliminated by day 7 with the SRF formulation vs the triple antibiotic without SRF which took 9 days to resolve. See FIG. 1. Other antibiotics tested in this manner included, Mupericin, neomycin bacitracin, polymyxin kanamycin, streptomycin, erythromycin, clindamycin, penicillin G, penicillin V, Ampicillin amoxicillin, tetracycline, chlortetracycline, oxytetracycline, doxycycline, cephalexin, cephalothin, chloramphenicol, and clindamycin, and several others.

Figure 1:
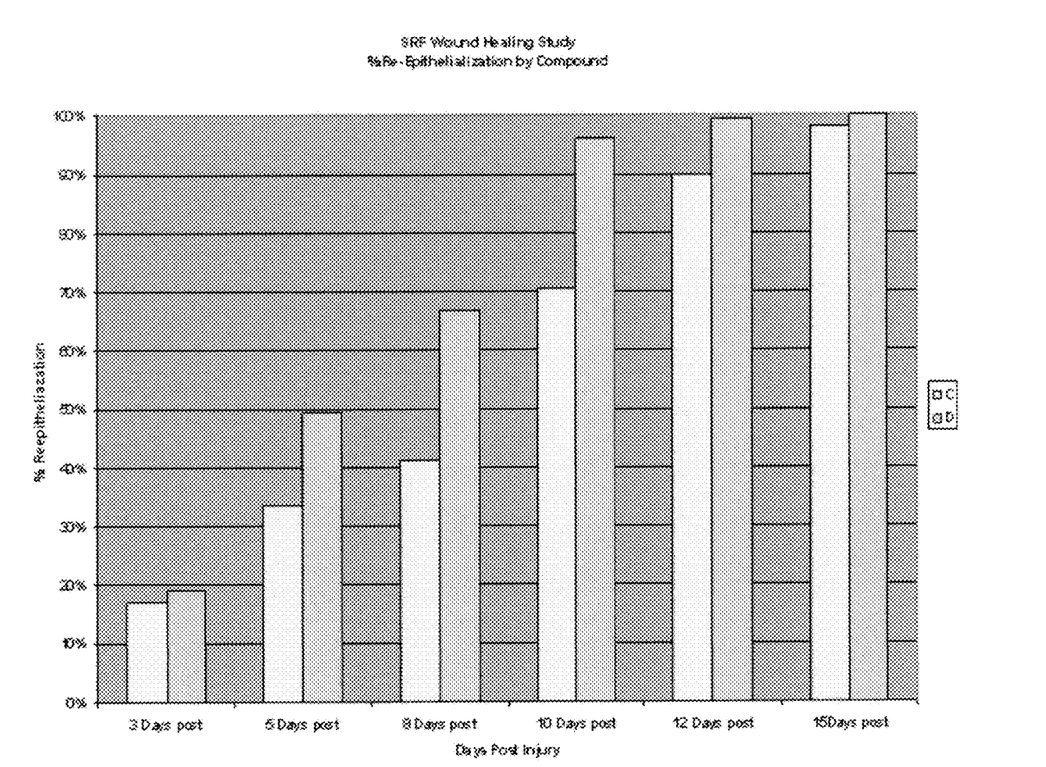
FIG. 1 shows a chart of a present invention wound healing study, % re-epithelization in 25 subjects.

As shown the triple antibiotic, Neosporin with SRF (2% of calcium pyruvate, 2% of magnesium pyruvate, 1% of L proline, and 1% of L citrulline) (D, Right Column) healed 2-3 days faster than the triple antibiotic without SRF Neosporin (C, left column) in infected wounds. Formula (D) contained SRF, in a triple antibiotic formula Neosporin.

Example 12 Fungal Infected Wounds

In this experiment, various antifungals were tested for their ability to kill an infection. The antifungal agents included the following medicaments: miconazole, chlotrimizole, tioconazole, terconazole, povidone-iodine, and butoconazole. In these experiments, SRF was placed into commercial antifungals formulations and were evaluated for enhanced efficacy. The patients reported that their fungal infections, including athlete's foot, jock itch and some skin infections cleared faster than their use of the commercial formulation.

Example 13. Treatment of Decubitus, Pressure Sores, Venous Status Ulcers and Wounds that do not Heal The reason wounds do not heal is due to many reasons like underlying disease states, poor nutrition and age. Protein deficiency impairs wound healing since protein is needed for fibroblast proliferation, new blood vessel formation, and collagen production. Protein deficiency leads to impaired healing through impaired collagen synthesis and deposition, decreased skin and facial wound-tensile strength. In addition to the clear role of protein intake in wound healing, proteins are essential to function of the immune system.

To the SRF formula of containing zinc pyruvate we added Arginine which is an essential amino acid and is involved in collagen synthesis of the healing wounds. At times of stress or injury, arginine synthesis is insufficient to meet the demands of increased protein turnover and the body arginine stores decrease rapidly. It is during these times that arginine becomes an indispensable amino acid in the process of wound healing. Like arginine, calcium pyruvate increases the synthesis of Nitric Oxide and cytokines needed to kill bacterial and virally infected cells. Nitric oxide is produced by the human body to kill infections. The beneficial effects of Nitric Oxide on wound repair may be its functional influences on angiogenesis, inflammation, cell proliferation, matrix deposition, and remodeling. Nitric oxide levels were increased by 42% at wound sites when SRF was applied. When tested on non-healing wounds, on various patients, the formula enhanced healing allowing all 6 patients to achieve complete healing of the nonhealing wound in 14-28 days.

Example 14 Eczema and Psoriasis

Ten patients with varying forms of Eczema were given an emollient cream with the SRF formula, containing 2% colloid oatmeal to test for one month. These patients used various forms of products and were asked to compare the SRF formula to their current product. 9 out of 10 patients rated the SRF formula superior to their current product including products with steroids. We also purchased the Neosporin essentials products used to treat eczema. We added the SRF (2% of calcium pyruvate, 2% of magnesium pyruvate, 1% of L proline, and 1% of L citrulline) formula to the two products, the daily moisturizing cream with colloidal oatmeal and to their 1% hydrocortisone anti-itch formula. The patients were asked to rate the products after seven days of use. They tested the non modified Neosporin products on two of five locations on the same arm. The other two spots were used to test the modified SRF product and one was used as an untreated control. The four locations were picked randomly and the test products were blinded. Each patient served as their own control. The results were evaluated on a 1-10 scale for resolution of the symptoms by the patient and the expert evaluator. The results were tabulated for all 10 patients in table 5 as percentage of reduction of symptoms.

See Table V.

TABLE V

Reduction Of Itching, Skin Irritation, Inflammation & Rashes With And Without SRF.

| Formula | % Reduction of itching | % Reduction of skin irritation | % Reduction of inflammation | % Reduction of rash |
|---|---|---|---|---|
| Untreated control | 10% | 5% | 0 | 0 |
| Neosporin Oatmeal Non modified | 20% | 30% | 25% | 29% |
| Neosporin Oatmeal With SRF | 60% | 70% | 55% | 60% |
| Neosporin Hydrocortisone Nonmodified | 70% | 75% | 80% | 80% |
| Neosporin Hydrocortisone With SRF | 90% | 92% | 100% | 96% |

Topical antihistamines and topical steroids have been used for years to reduce skin inflammation. The problem is that they do not improve healing and, in some cases, prolong the healing process of injured skin. The average days to healing with these products is around 18 days. The addition of SRF to these commercial creams or lotions decreased the days to healing to 12 days a 34% increase in healing. The antihistamines tested were diphenhydramine, doxepin, and the topical steroids tested were aclometasone, fluocinolone, hydrocortisone, desonide, mometasone, prednicarbate, triamcinolone, amcinonide, diflorasone, betamethasone and clobetasol. Patients with severe psoriasis requiring the use of immunosuppressant's were treated topically with SRF that contained 3-Bromopyruvate which produced dramatic results in resolving severe psoriasis.

SRF increases the synthesis of Nitric Oxide (NO) to enhance the rate of healing and kill infections. Nitric oxide is released in the skin after exposure to sunlight and this molecule can help reduce the inflammation. This in turn leads to reduction of the itching symptoms that leads to such distress among the persons suffering from eczema. Several techniques can be used to measure nitric oxide in intact skin. The intracellular nitric oxide assay uses a fluorescent probe for direct nitric oxide detection in live intact cells. The nitric oxide-specific probe is extremely photostable and provides a wide pH stability range of 5.5 to 9.0. Also, an invitro nitric oxide assay measures nitric oxide indirectly via the breakdown products of nitric oxide (nitrite and nitrate) in cell lysates, tissue homogenates, plasma, serum, saliva, urine, and cell culture supernatants. Assays are available for either colorimetric or fluorometric detection in a 96-well plate.

For this study the team of researchers exposed some healthy volunteer participants to SRF, on a small patch of eczema skin. On testing they noted presence of nitric oxide in their blood stream as a result of this exposure and an increase in skin nitric Oxide. Mean basal NO concentration measured in vivo, in twenty-one dialysis probes in twenty-one subjects were 0-49+0 06/M. Following intradermal injection of Pyruvate, NO concentration in the dialysate from the weal response increased to a maximum of 1*68+ 0-16/LM within 2 min (P<0.0002). Following intradermal injection of SRF, NO concentration in the dialysate from the weal response increased to a maximum of 2*38+0-16/LM within 2 min (P<0.0002). In the flare area, NO levels rose to 1 19+0-26/SM (P<0.018) at 6-8 min after SRF injection, the maximum level coinciding with the flare front crossing the dialysis probe. The mean areas of the weal and flare responses were 2-3+0 3 cm2 and 19 5+1-7 cm2 (n=6) respectively. No significant increase in NO was detected following intradermal saline.

Nitric oxide in turn was noted to activate some specialized immune cells called the regulatory T cells. These cells kill the hyperactive inflammatory responses that lead to the symptoms of eczema in the first place. Nitric Oxide also turns off N F kappa B the major inflammatory gene in humans. NO is an important regulator and mediator of numerous processes in the nervous, immune, and cardiovascular systems. These include vascular smooth muscle relaxation, resulting in arterial vasodilation and increasing blood flow. NO is also a neurotransmitter and has been associated with neuronal activity. NO also partially mediates macrophage cytotoxicity against microbes and tumor cells.

TABLE VI

Testing various topical wound healing formulas for production of Nitric oxide (NO) and days to healing wounds with SRF or without certain SRF components (2% calcium and 2% magnesium pyruvate, 1% L proline and 1% L-citrulline) in wounded hairless Rats compared to non-wounded normal skin.

| Formula | Days to healing | % of NO levels against normal nonwounded skin |
|---|---|---|
| Normal non wounded skin | 0 | 100% |
| Untreated control | 19 | 20% |
| Vehicle Petrolatum | 16 | 18% |
| Calcium pyruvate without L proline Or L-citrulline | 15 | 22% |
| Calcium pyruvate with L proline | 16 | 23% |
| Calcium pyruvate with L-citrulline | 15 | 31% |
| Calcium pyruvate with L proline And L-citrulline | 14 | 34% |
| Magnesium pyruvate without L proline Or L-citrulline | 13 | 36% |
| Magnesium pyruvate with L proline | 15 | 38% |
| Magnesium pyruvate with L-citrulline | 16 | 45% |
| Magnesium pyruvate with L proline And L-citrulline | 14 | 51% |
| Magnesium pyruvate and Calcium pyruvate without L proline Or L-citrulline | 16 | 46% |
| Calcium pyruvate and Magnesium pyruvate alone With L-citrulline | 13 | 52% |
| Calcium pyruvate and Magnesium pyruvate with L Proline But without L-citrulline | 15 | 37% |
| Calcium pyruvate and Magnesium pyruvate with L- Proline and with L-citrulline (SRF) | 11 | 88% |

Example 15

Various commercial lotions and creams were purchased to evaluate these formulas with and without SRF in patients that purchased them. The products included Gold Bond pain and itch relief cream, Gold bond ultimate skin protectant lotion, Gold bond ultimate restoring skin therapy lotion, gold bond ultimate softening lotion, and Gold bond ultimate healing Aloe skin therapy lotion and Gold Bond eczema formula. 143 patients were asked to evaluate the modified formula with SRF on a 1-10 scale, with 1 being worse than their current product, 5 being equal and 10 being far superior to the current product without SRF. The patients used the modified SRF product for one month and 109 returned the questionnaire with an overall rating of a 7.8 for the SRF containing products with an overall rating of 8.2 for likely purchase, compared to the rating of 4-6 for the other products without SRF.

Example 16 Pigmentation Study

Six laser wounds were made on the left arm. As an example, Mupirocin was placed on the first wound site, Mupirocin plus sodium pyruvate was placed on the second wound site and Mupirocin with SRF was placed on third wound site. The same process was repeated with another drug for sites 4-6. Every two days the bandages coated with the drugs were removed and replaced five times. Pigmentation measurements range from 1-10 with 10 being totally normal. The mupirocin drug formulas averaged a 4.9 for pigmentation. The addition of sodium pyruvate raised that to 6.0, an increase of 18% for pigmentation. The addition of the SRF averaged 7.45 a 34% increase in pigmentation.

Example 17: Cancer Drugs Damage Normal Cells and Organs and Inhibit the Synthesis of Nitric Oxide The use of SRF offers promise in battling cancer-related deaths in the United States by decreasing hypoxemia at cancer sites and increasing the synthesis of nitric oxide to enhance the cellular death of cancer with and without cancer drugs.

Hypoxia within regions of solid tumors including lung cancers, is associated with resistance to standard treatments, particularly radiotherapy. Conventional drug therapy, which depends on reaching the cancer through the bloodstream, can be less effective in hypoxic tumors. Low oxygen levels in a cell interrupt the activity of oxidative phosphorylation, a term for the highly efficient way that cells normally use to convert food to energy. As oxygen decreases, the cells switch to glycolysis to produce their energy units, called ATP. Glycolysis is a drastically less efficient way to obtain energy, and so the cancer cells must work even harder to obtain even more food, specifically glucose, to survive. When oxygen levels dip dangerously low, angiogenesis, or the process of creating new blood vessels, begins. The new blood vessels provide fresh oxygen, thus improving oxygen levels in the cell and tumor and slowing the cancer growth—but only temporarily.

Drug designers have taken advantage of the hypoxic regions in tumors and designed anticancer drugs that are specifically active or activated under hypoxic conditions. For example, hypoxia-activated prodrugs like 3-bromopyruvate, are chemically modified to be inactive, but when administered to the body and exposed to hypoxic conditions (such as in a tumor including skin cancer), they are metabolized or otherwise converted into the active, anticancer form. Despite these new drugs, there is an ongoing need for innovative approaches to anticancer therapy.

Example 18: Pretreatment of Normal Cells Co Cultured with Cancer Cells, Followed by Treatment with Doxorubicin Peripheral blood monocytes and U937 monocytic leukemia tumor cells were placed in sterile culture flasks and maintained in culture using Dulbecco's Minimal Essential Medium, with 10% fetal calf serum, supplemented with 2 mM glutamine and Pen/Strep. The cytotoxicity of the cytotoxic agent on the cells was analyzed by propidium iodide exclusion techniques and flow cytometric quantitation. Viability of the cells was quantified as the number of cells that excluded the vital dye trypan blue. SRF was dissolved in distilled water and the solution was adjusted to pH 7.4. Solutions were sterile filtered. Stock solutions were prepared so that the vehicle would not be more than 1% of the total volume of the culture media. In H-Thymidine Radiosotopic Incorporation Measurement of cytotoxicity, SRF was examined for its ability to decrease the cytotoxicity of Doxorubicin to U937 monocytic leukemia cells and normal peripheral blood monocytes. The optimal concentrations of the agents that were able to protect cells against Doxorubicin induced cytotoxicity were the 0.1% calcium pyruvate, 0.1% magnesium pyruvate, 0.1% L-proline, and 0.1% L-citrulline (SRF). Susceptibility studies were conducted to determine the optimal treatment time of the cells with the cryoprotective agents prior to treatment of the cells with the cytotoxic agent. The normal cells and U937 leukemic tumor cells were pretreated separately in "wash out" studies with the single agents alone, and in combination, at the optimal concentration described above for various time periods, washed with fresh medium to remove the agents, and treated with the cytotoxic agent. The co-culture of normal and U937 leukemic minor cells was treated essentially in the same manner except that the cells were not treated separately, but co-cultured. The optimal pretreatment time of the cells with SRF found to be 24 hours prior to treatment of the cells with Doxorubicin. The cells were then placed in culture medium without the protective agents. The length of time that the cryoprotection lasted was 24 hours following Doxorubicin treatment. At this time, peripheral cell viability is a limiting factor because these cells are normal cells and do not remain in culture for extended periods of time.

Normal and U937 tumor cells were co-cultured and the cytotoxicity of Doxorubicin on the cells was determined by viability assays which examined the differential ability of the cytoprotective compositions alone, and in combinations, to protect the normal cells from the cytotoxicity of the chemotherapeutic agent.

The cells were isolated and examined for morphological evidence of cytotoxicity or prevention of cytotoxicity. These studies determined the cytoprotective effect of SRF on the normal and tumor cells. DNA synthesis studies using 3H-thymidine (1 uCi/well) were carried out 4 hours prior to termination of the experiment to determine the effect of the formulations on the proliferation of the cells as a measure of the prevention of cytotoxicity and the extent of Doxorubicin-induced cytotoxicity. Propidium iodide exclusion analysis was carried out for direct quantitation of the cytotoxicity and the prevention of cytotoxicity. Each set of studies was performed in triplicate so that statistical analysis of the significant differences between the treatment groups could be conducted.

SRF provided significant protection to the normal peripheral monocytes and did not protect the tumor cells from the effects of the Cytotoxic agent. Wash-out studies were conducted to determine viability of the peripheral blood monocytes co-cultured with U937 monocytic leukemia cells after 24 hour pretreatment of the cells with SRF, which is also a mitochondrial protective agent, followed by administration of Doxorubicin. The viability of the control normal peripheral cells was enhanced from 55% to 68% with the use of SRF, whereas the viability of the control U937 cells was decreased from 43% to 12%. Thus the use of SRF protected normal cells for 24 hours, while the leukemia cells died.

See Table VIII.

TABLE VIII

Comparison of various cancer drugs in various media.
Percentage of viable non-cancerous cells after incubation with anticancer drugs

| Various Drugs | Percentage of viable cells after incubation with drugs | Drugs in commercial formula | Drugs in commercial formula sodium pyruvate without SRF | Drugs in commercial formula with SRF | Drugs in commercial formula with SRF repeat study |
|---|---|---|---|---|---|
| anastrozole | 24 | 25 | 50 | 86 | 94 |
| Bleomycin | 31 | 33 | 47 | 98 | 98 |
| cisplatin | 46 | 43 | 58 | 88 | 91 |
| Carboplatin | 42 | 50 | 56 | 87 | 97 |
| floxuridine | 38 | 38 | 58 | 92 | 91 |
| methotrexate | 42 | 43 | 68 | 94 | 98 |
| oxaliplatin | 23 | 24 | 41 | 95 | 98 |
| Bevacizumab | 21 | 27 | 40 | 88 | 87 |

Other drugs tested produced similar results as stated in the above table. They included Crizotinib, Docetaxel, Erlotinib, Etoposide, Gemcitabine, Irinotecan, Paclitaxel, Pemetrexed, Vinorelbine.

Example 19: Treatment of Patients with Various Cancers

To date most patients with cancer that are treated with radiation or cancer drugs show a partial reduction of tumor sizes, but in most cases the cancer remains and life expectances increases for a short period of time. This is the case for tumors. Five patients with various cancers were treated with 3-Bromopyruvate, an alkylating agent and a well-known inhibitor of energy metabolism. Results to date have been mixed. The problem with most cancer drugs is not only their toxicity to noncancerous tissue, but is their inability to completely eradicate the cancer. Cancer drugs cause hypoxia in normal noncancerous cells and they destroy tissue and their ability to heal. In mice studies conducted by others, they investigated the chemo preventive activity of 3-bromopyruvate. For the topical treatment the mice were treated with 10-30 mg/5 ml daily and treated for 8 weeks. 3-bromopyruvate significantly decreased tumor multiplicity and tumor load by 40% and 60%, respectively, at a dose of 10 mg/5 mL. Treatment with 3-bromopyruvate in tissue cultures of cancer cells showed an increased immune histo chemical staining for cleaved caspase-3, suggesting that the tumor inhibitory effects of 3-bromopyruvate were through induction of apoptosis. 3-Bromopyruvate also dissociated hexokinase II from mitochondria, reduced hexokinase activity, and blocked energy metabolism in cancer cells, finally triggered cancer cell death and induced apoptosis through caspase-3, and PARP in human lung cancer cell line. The problem with 3-bromopyruvate was its toxicity to normal cells. The formula needed to protect noncancerous cells from 3-bromopyruvate and to enhance its effect on tumors, was the addition of SRF 1-2 hours prior to the administration of the 10 mg of 3-bromopyruvate. The investigators were given SRF formula 1-2 hours prior the treatment of the cancer drug. This approach reduced tumor sizes by 90% compared the 60% reduction with 3 bromopyruvate by itself. The addition of dichloroacetate with 3-bromopyruvate to the SRF formula was the best formula decreasing tumor loads by 95%, especially with the addition of magnesium bicarbonate that increased the PH to 7.9 to neutralize the lactic acid produced in tumors that enhance tumorigenesis.

Example 21: Cancer Trial Pilot Study

In eleven patients with various cancers, were given The SRF, which increased Nitric oxide levels in these patients to enhance the effect of the chemotherapy or radiation, and protected normal cells and help reduce hypoxia in cancer cells.

These patients applied the SRF to the topical cancer or injected it into the tumors. one to two hours before they were treated with cancer drugs or radiation, given by current standard methods. These patients continued chemo therapy beyond the eight weeks and ten patients are still alive six to 10 years later, beating the national survival rate by 4 years.

Other drugs tested given by IV or oral or topically, standard treatments reduces tumor sizes or loads by an average 29.2% as sited in the literature. These drugs were Crizotinib, Docetaxel, Erlotinib, Etoposide, Gemcitabine, Irinotecan, Paclitaxel, Pemetrexed, Vinorelbine.

Example 22 Tissue Culture Studies of Herpes Simplex HSV-1 or 2 or Human Papillomavirus HPV To investigate the ability of SRF to regulate the inflammatory process during an infection, the MatTek EpiDerm Assay was used. The MatTek Epiderm tissue samples were treated with SRF and the combination with immunostimulators Imiquimod and antiviral agents Acyclovir determine if the combination would regulate nitric oxide, IL-1 and IL-8 up or down during a simulated infection. Following a one-hour equilibration, the Epiderm tissues were placed into the incubator (37° C., 5% $CO_2$) in assay medium. The old medium was replaced with fresh medium and the test articles were applied to the tissue samples. The test articles remained in contact with the tissue for various dosing times, one hour, then at four hours, and at 20 hours. The testing was run in duplicate. Various immunostimulators Imiquimod or sodium dodecyl sulfate (SDS), glycoprotein D (gpD) were used singly or with the SRF to replicate an infection, along with vehicle controls. Untreated samples were used as negative controls. Following treatment, the media from the tissue samples were tested in Elisa kits for IL-1 and IL-8 according to the manufacture's protocols.

Results: The primary end points were the levels of IL-8 and IL-1 after treatment with an immunostimulators, and SRF. The immunostimulators did not increase the cytokines by themselves. This model did not have white blood cells to respond to the immunostimulators or produce oxygen radicals. The immunostimulators in combination with SRF increased Nitric oxide, and IL-8 over 400%, which shows direct antimicrobial activity, compared to the untreated controls. IL-8 activates neutrophils to increase their numbers at the infected site. In the same experiment, IL-1 was decreased significantly (over 300%). IL-1 increases inflammation and decreases healing times. This test clearly showed that SRF and the immunostimulators regulated the inflammatory process in dermal tissues in a manner that would increase the body's ability to fight infected wounds and increase the body's ability to healing quicker. The same experiment was done with virally infected cells and the SRF in combination with immunostimulators decreased viral plaque formed by HSV-1 or 2 by 70% and HPV-18 decreased by 82%. Viral plaques are a direct measure of viral numbers in infected cells. The antiviral drug, Acyclovir also decreased viral HIV plaques by 60% and SRF with an immunostimulators and acyclovir, totally eliminated the virus from the infected cells.

Percentage of Viral Plaque Reduction in Virally Infected Cells in Humans

A total of 15 patients with vaginal HPV 16 or 18 were treated with the SRF cream that also contained imiquimod. The results clearly show that SRF and Imiquimod increased inflammatory cytokines high enough needed to kill high numbers of the virus in virally infected cells as measured by reduction in viral plaques. Imiquimod normally reduced viral plaques in virally infected cells by 25-40%. SRF reduces viral plaques in virally infected cells by 22-34%. Unexpectedly, the combination of SRF and Imiquimod produced the best results, by reducing the viral plaques over 92%, eliminating the virus from most of the infected cells. This tissue culture data along with data from humans, confirms that this combination worked.

Example 23 Lip Plumping Products the Addition of SRF Increases Collagen Deposition and Added Better Moisturizing to the Lips Alpha-Keto-glutarate is taken up by lip cells to increase collagen deposition by fibroblasts. In combination with SRF, Alpha-keto-glutarate produced the greatest results. This product will plump up the lips and increase their thickness by increasing collagen deposition. When you need a fast fix for thin lips, this moisturizing gloss immediately stimulates your kisser with cinnamon, peppermint and ginger to trigger plumping and flushing with a hint of color and shine. Full, smooth & kissable soft. Plumping agents used are cinnamon, capsaicin, caffeine, ginger, menthol, niacin and vitamin A.

Example 24 Post Waxing or Shaving Product

Brazilian Chill Post shaving gel with SRF produced a superior product. It reduces the number of ingrown hair, razor bumps, and redness from shaving, waxing, electrolysis or laser hair removal and is great for women after shaving legs, bikini lines and underarms as well as for men who see redness after shaving their faces. SRF reduces the redness, erythema and pain. SRF reduced redness, pain erythema that other products do not provide. SRF also increases healing of sore irritated skin. Acetylsalicylic Acid—active ingredient that unblocks pores and soothes skin.

Example 25 Cellulite

Cellulite is a skin condition found in 90% of women over 30 years of age. Skin adipocytes undergo hypertrophy and hyperplasia thus cellulite is characterized by large stable adipocytes that are limited to the lower body area. Many techniques have been tried, but to date no real effective treatment exists. L arginine, cinnamon oil, methylsulfonylmethane have been tried with little success. Stimulating Nitric oxide is effective to prevent and reduce cellulite, reduce inflammation and increase microcirculation. SRF was used in conjunction with Vitamin A palmitate (retinol) acetyl dipeptide-1 cetyl ester, L arginine, palmitoyl pentapeptide, sodium hyaluronate in the Genederm deliver formula. In tests on 9 women with cellulite the SRF formula reduced cellulite by 30% in a month as measured by photo imaging. In three months, the cellulite was reduced by 56% as averaged over the 9 women treated.

The invention being thus described; it will be obvious that the same may be varied in many ways. Such variations are not to be regarded as a departure from the spirit and scope of the invention and all such modifications are intended to be included within.

What is claimed is:

1. A topical medicinal composition for treatment of mammalian cells, comprising a topically pharmaceutically effective amount of each of the following constituents:
 a) magnesium pyruvate;
 b) calcium pyruvate;
 c) L proline;
 d) and citrulline; and
 e) a liquid carrier;
 wherein said L proline is in the amount of about 0.1% to about 3.0%, based on total weight of the composition, and wherein said citrulline is selected from the group consisting of L citrulline, citrulline malate and combinations thereof, and said citrulline is in the amount of about 0.1% to about 3.0%, based on total weight of the composition.

2. The medicinal composition of claim 1 wherein said magnesium pyruvate and said calcium pyruvate are each in the amount of about 0.1% to about 5.0%, based on total weight of the composition.

3. The medicinal composition of claim 2 wherein said magnesium pyruvate and said calcium pyruvate are each in the amount of about 0.2% to about 4.0%, based on total weight of the composition.

4. The medicinal composition of claim 3 wherein said magnesium pyruvate and said calcium pyruvate are each in the amount of about 0.5% to about 4.0%, based on total weight of the composition.

5. The medicinal composition of claim 1 wherein said L proline and said citrulline are each in the amount of about 0.2% to about 2.5%, based on total weight of the composition.

6. The medicinal composition of claim 1 wherein said composition has a carrier selected from the group consisting of water, oil, water-based carriers, oil-based carriers, gels, emulsions, lotions, creams, solutions and petrolatum.

7. The medicinal composition of claim 1 wherein said composition includes at least one additional active constituent that is selected from the group consisting of antioxidants, antibacterial agents, alpha-keto acids, antiviral agents, antifungal agents, antihistamine agents, cancer drugs, HIV drugs non-steroidal anti-inflammatory agents, antioxidant agents, fatty acids, steroids, and mixtures thereof.

8. The medicinal composition of claim 7 wherein said alpha-keto acids have four or more carbon atoms and are selected from the group consisting of oxaloacetate, alpha-keto-glutarate, alpha-keto-isovalerate, alpha keto-butyric acid, alpha keto-adipic acid, alpha-keto-caproic acid, salts thereof, and mixtures thereof.

9. A topical treatment method for treatment of mammalian cells for enhancing the synthesis of collagen, adhesion molecules, and elastin to increase wound strength, wound texture, pigmentation and nitric oxide, wherein the wounds and diseases are selected from the group consisting patients with wrinkles, aging skin, cellulitis, wounds and diseases which are selected from the group consisting of infected and noninfected wounds, bacterial infections, fungal infections, viral infections, cold sores, thermal burns, sunburns, chemical burns, surgical wounds, psoriasis, eczema, decubitus ulcers, cancer, diabetic ulcers, dermatoses, inflammatory diseases, and wounds resulting from laser treatment, micro-wounded skins, scratches, micro-needling, abrasions, laceration, puncture, dry skin, contact with irritants, contact with allergens or other substances that are harmful to skin or skin cells, which comprises:

applying a therapeutically effective amount of a medicinal composition topically to mammalian cells, said medicinal composition including: a) magnesium pyruvate; b) calcium pyruvate; c) L proline; d) citrulline; and e) a liquid carrier;

wherein said L proline is in the amount of about 0.1% to about 3.0%, based on total weight of the composition, and wherein said citrulline is selected from the group consisting of L citrulline, citrulline malate and combinations thereof, and said citrulline is in the amount of about 0.1% to about 3.0%, based on total weight of the composition.

10. The method of claim 9 wherein said magnesium pyruvate and said calcium pyruvate are each in the amount of about 0.1% to about 5.0%, based on total weight of the composition.

11. The method of claim 10 wherein said magnesium pyruvate and said calcium pyruvate are each in the amount of about 0.2% to about 4.0%, based on total weight of the composition.

12. The method of claim 11 wherein said magnesium pyruvate and said calcium pyruvate are each in the amount of about 0.5% to about 4.0%, based on total weight of the composition.

13. The method of claim 9 wherein said L proline and said citrulline are each in the amount of about 0.2% to about 2.5%, based on total weight of the composition.

14. The method of claim 9 wherein said composition has a carrier selected from the group consisting of water, oil, water-based carriers, oil-based carriers, gels, emulsions, lotions, creams, solutions and petrolatum.

15. The method of claim 9 wherein said at least one additional active constituent is included in the composition that is selected from the group consisting of antioxidants, antibacterial agents, alpha-keto acids, antiviral agents, antifungal agents, antihistamine agents, cancer drugs, HIV drugs non-steroidal anti-inflammatory agents, antioxidant agents, fatty acids, steroids, and mixtures thereof.

16. The method of claim 7 wherein said alpha-keto acids have four or more carbon atoms and are selected from the group consisting of oxaloacetate, alpha-keto-glutarate, alpha-keto-isovalerate, alpha keto-butyric acid, alpha keto-adipic acid, alpha-keto-caproic acid, salts thereof, and mixtures thereof.

* * * * *